United States Patent [19]
Ice et al.

[11] Patent Number: 5,728,310
[45] Date of Patent: Mar. 17, 1998

[54] MICROWAVE WASTE STERILIZER AND METHOD OF USE

[75] Inventors: Charles L. Ice, Grapevine, Tex.; John V. McCullough, Santa Cruz, Calif.

[73] Assignee: Forward Systems Automation, Grand Prairie, Tex.

[21] Appl. No.: 510,287

[22] Filed: Aug. 2, 1995

[51] Int. Cl.⁶ ............................................. H05B 6/72
[52] U.S. Cl. .................... 219/679; 219/697; 219/696; 219/686; 219/756; 219/748; 219/750; 219/762; 422/21; 588/900
[58] Field of Search ............................ 219/695, 696, 219/697, 701, 686, 679, 746, 748, 750, 756, 762, 704, 707; 422/21, 307; 588/212, 227, 900

[56] References Cited

U.S. PATENT DOCUMENTS

| | | | |
|---|---|---|---|
| 2,593,067 | 4/1952 | Spencer | 219/746 |
| 3,110,794 | 11/1963 | Sale | 219/695 |
| 3,210,511 | 10/1965 | Smith | 219/697 |
| 4,006,338 | 2/1977 | Dehn | 219/697 |
| 4,035,598 | 7/1977 | Van Amsterdam | 219/697 |
| 4,276,462 | 6/1981 | Risman | 219/746 |
| 4,477,707 | 10/1984 | Kim | 219/897 |
| 4,683,363 | 7/1987 | Scovell | 219/686 |
| 5,124,125 | 6/1992 | Brent | 422/21 |
| 5,180,895 | 1/1993 | Briggs et al. | 219/697 |
| 5,223,231 | 6/1993 | Drake | 422/297 |
| 5,457,303 | 10/1995 | Shute et al. | 219/695 |

FOREIGN PATENT DOCUMENTS 54-16745  2/1979  Japan ........................... 219/695

OTHER PUBLICATIONS

"All Medical Waste Disposal Systems" brochure.
"Roatan—The Alternative—Medical Waste Disposal" brochure.

*Primary Examiner*—Philip H. Leung
*Attorney, Agent, or Firm*—Wendy K. Buskop; Chamberlain, Hrdlicka et al.

[57] ABSTRACT

There is provided a microwave waste sterilizer comprising an upper outer shell, a lower outer shell, an upper means for guiding microwave energy, a lower means for guiding microwave energy, an upper means for dispersing microwave energy, and a lower means for dispersing microwave energy. There is also provided a method for sterilizing waste materials with dual sources of microwave energy. Further there is provided a method for dispersing microwave energy into a chamber such that the dispersed microwave energy creates a flux field of substantially uniform flux.

30 Claims, 8 Drawing Sheets

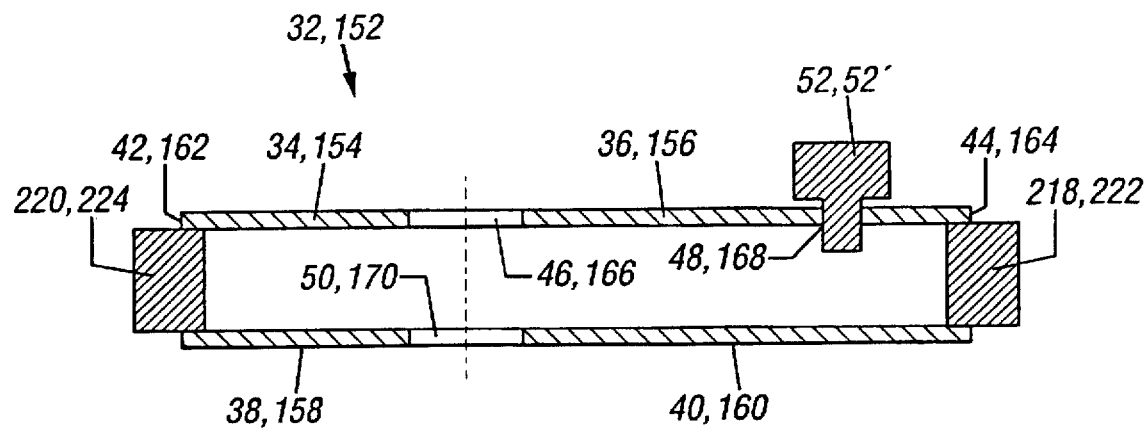
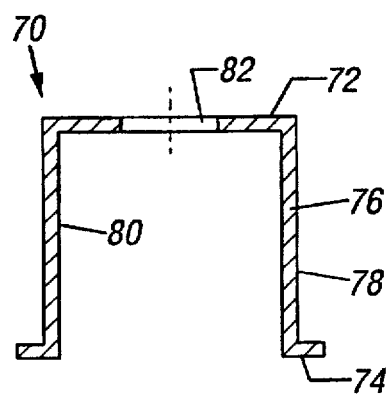
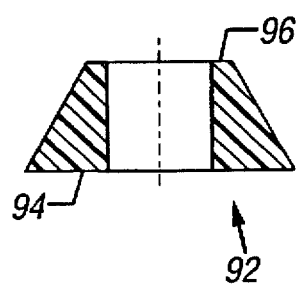
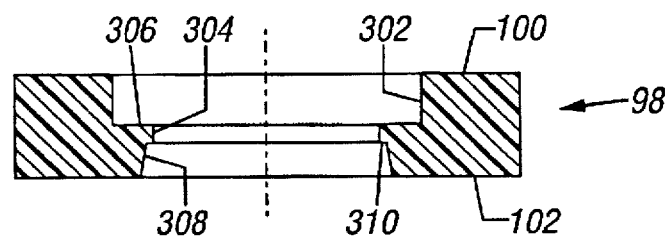

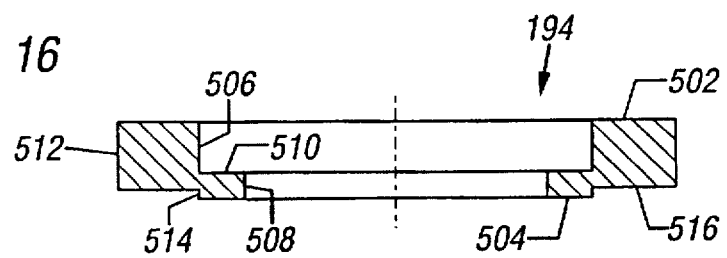
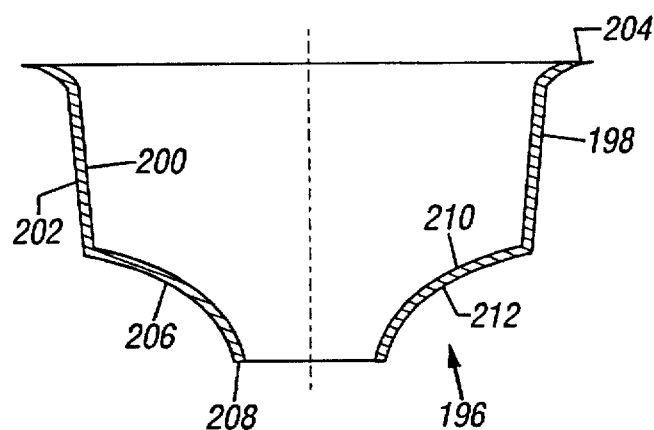
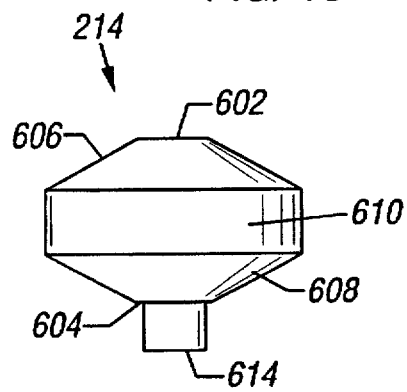
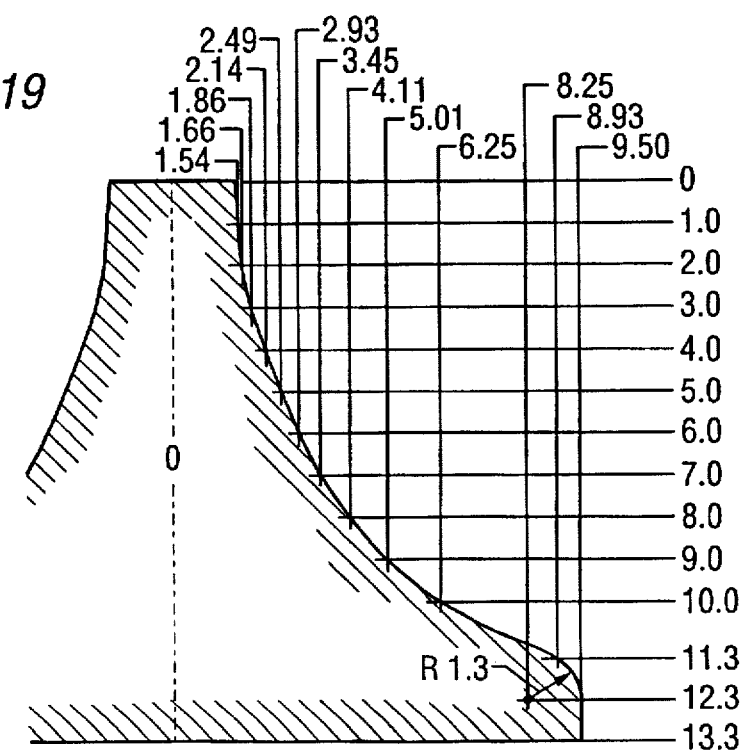

5,728,310

MICROWAVE WASTE STERILIZER AND METHOD OF USE

BACKGROUND OF THE INVENTION

In one aspect the invention relates to a device to sterilize waste. In another aspect, the invention relates to waste sterilization by microwaves. In yet another aspect, the invention relates to a method for dispersing microwaves in a substantially uniform pattern.

Sterilization devices which use microwave energy are not new. One type of microwave sterilizer functions like a microwave ovens wherein the load is placed in a tuned chamber. Another type of microwave sterilizer, such as Drake, U.S. Pat. No. 5,223,231, functions as an autoclave. Unfortunately, these type of devices decrease the efficiency of the microwave chamber so that substantially less than half of the energy broadcast from the magnetron is utilized. A waste sterilizer that utilizes a greater percentage of the available microwave energy would be highly desirable.

Microwave energy is known to be able to generate heat. Microwaves have been used for cooking and melting. Brent, U.S. Pat. No. 5,124,125 used microwave energy to heat waste and plastics together to simultaneously sterilize and encapsulate. New plastics must be used each time the device is used. A sterilization process that allows waste containers to be reused would be very desirable.

Many times microwave sterilizers require a large amount of water. The water must then be drained and treated at the end of a cycle. A sterilization process that uses less water and which can recycle the water for the next cycle would be desirable.

Many microwave sterilizers, such as microwave autoclaves, inject pressure into the vessel. Consequently, the vessel will contain cold spots, or areas where the vessel is not at the temperature desired. A microwave sterilizer that generates all pressure internally due to internal temperature, thus eliminating cold spots, would be desirable.

Microwaves are generally broadcast and tuned such that the heating or cooking pattern is uneven. A method whereby the microwave energy could be dispersed in a fairly uniform pattern would be desirable.

OBJECTS OF THE INVENTION

It is an object of the invention to provide a microwave waste sterilizer that is highly efficient in the use of the microwave energy which is broadcast.

It is further an object of the invention to provide a microwave waste sterilizer that allows waste containers used in the sterilization process to be reused.

It is still further an object of the invention to provide a microwave sterilization process that can recycle the moisture added and condensate formed during the process.

It is even further an object of the invention to provide a microwave sterilization process that generates all necessary pressure internally, thus eliminating cold spots.

It is yet another object of the invention to provide a process of introducing microwave energy into a chamber in a uniform and dispersed pattern.

SUMMARY OF THE INVENTION

In one embodiment of the invention there is provided a microwave waste sterilizer comprising an upper outer shell, a lower outer shell, an upper means for guiding microwave energy connected to the upper outer shell, a lower means for guiding microwave energy connected to the lower outer shell, an upper means for dispersing microwave energy connected to the upper means for guiding microwave energy, a lower means for dispersing microwave energy connected to the lower means for guiding microwave energy, and a clamp releasably holding the upper outer shell and the lower outer shell together.

In another embodiment of the invention there is provided a method for sterilizing waste materials. The method comprises placing waste materials in a reusable plastic waste container, placing the waste container in a microwave waste sterilizer, broadcasting an upper magnetron and a lower magnetron simultaneously so as to generate microwaves within the microwave waste sterilizer to heat the microwave waste sterilizer in the presence of water to a predetermined pressure, maintaining the pressure for a predetermined time period, stopping the generation of microwaves, releasing the pressure until near atmospheric conditions exist within the microwave waste sterilizer, opening the waste sterilizer; and removing the waste container.

In yet another embodiment of the invention there is provided a method for dispersing microwave energy into a chamber. The method comprises broadcasting microwave energy across a chamber, reflecting the microwave energy from a surface of the chamber, coupling the microwave energy onto a means for coaxial guidance, changing a first direction of flow of the microwave energy to a second direction of flow substantially parallel to the means for coaxial guidance, propagating the microwave energy in the second direction of flow within a means for guiding microwave energy, splitting the microwave energy in a means for dispersing microwave energy, and creating a flux field of substantially uniform flux.

BRIEF DESCRIPTION OF THE DRAWINGS

FIG. 8 is a cross-sectional view of the waveguide and magnetron.

FIG. 9 is a cross-sectional view of the upper z-neck.

FIG. 10 is a cross-sectional view of the conic support.

FIG. 11 is a cross-sectional view of the collar.

FIG. 16 is a cross-sectional view of the adaptor.

FIG. 17 is a cross-sectional view of the lower inner liner.

FIG. 18 is a cross-sectional view of the lower deflector.

FIG. 19 is a sectional view of the inside surface of a parabolic shaped bell, depicting a curvature of the inside surface.

DETAILED DESCRIPTION OF THE PREFERRED EMBODIMENTS

Figure 1:
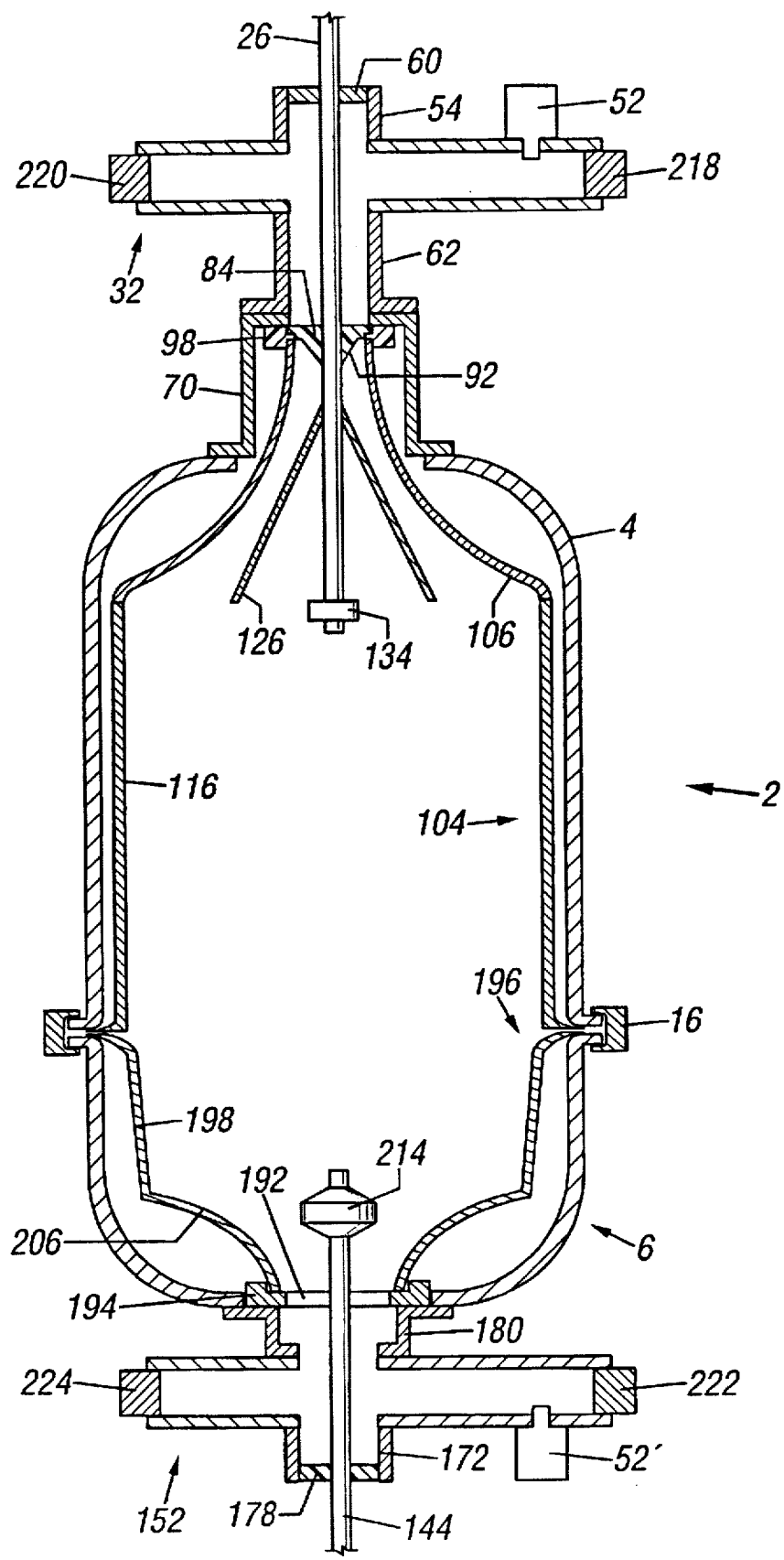
FIG. 1 is a cross-sectional view showing the sterilizer as assembled.

In one embodiment of the invention, with reference to FIG. 1–FIG. 18, there is provided a microwave waste sterilizer 2 for sterilizing items as numerous as infectious medical waste, contaminated food products and animal tissue. The microwave waste sterilizer comprises an upper outer shell 4, a lower outer shell 6, an upper means for guiding microwave energy 8 connected to the upper outer shell 4, a lower means for guiding microwave energy 10 connected to the lower outer shell 6, an upper means for dispersing microwave energy 12 connected to the upper means for guiding microwave energy 8, a lower means for dispersing microwave energy 14 connected to the lower means for guiding microwave energy 10, and a clamp 16 releasably holding the upper outer shell 4 and the lower outer shell 6 together.

Figure 6:
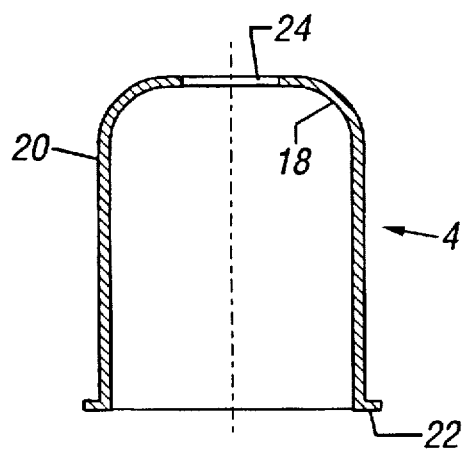
FIG. 6 is a cross-sectional view of the upper outer shell.
Figure 7:
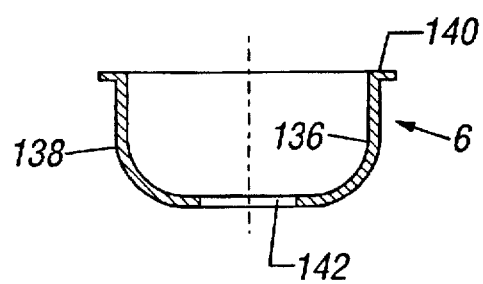
FIG. 7 is a cross-sectional view of the lower outer shell.

The upper outer shell 4, shown in FIG. 6, is generally bell shaped and has an inside surface 18, an outside surface 20, a flanged bottom end 22, a longitudinal axis, and a hole 24 at the apex of the bell shape. The hole 24 is coaxial with the longitudinal axis. The mating lower outer shell 6, shown in FIG. 7, is generally bowl shaped and has an inside surface 136, an outside surface 138, a flanged top end 140, a longitudinal axis, and a hole 142 at an apex of the bowl shape. This hole 142 is coaxial with the longitudinal axis of the lower outer shell. The ranged ends of the upper and lower outer shells are designed to be held together by the clamp 16 to form a pressure vessel.

Figure 2:
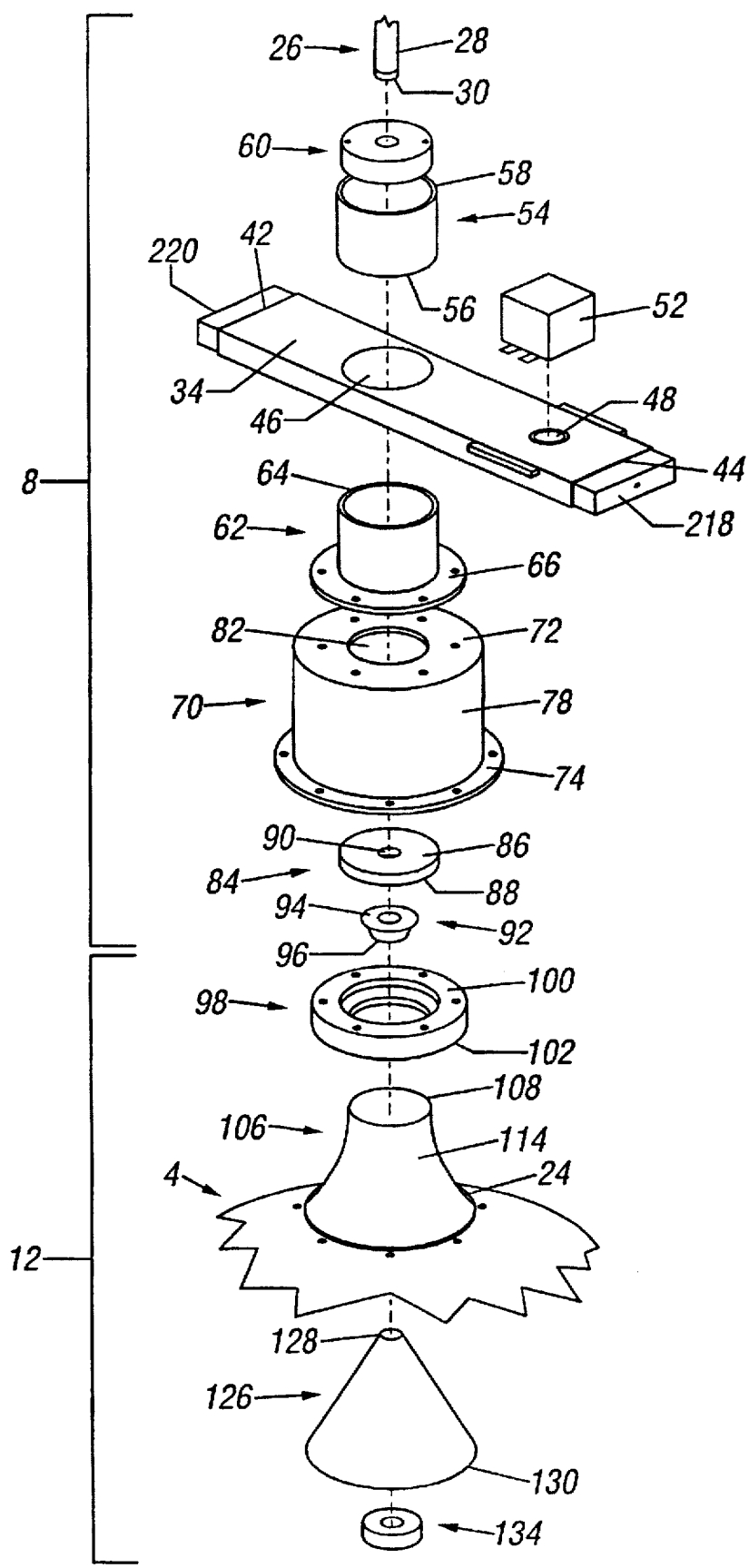
FIG. 2 is an exploded view of the upper sections.

FIG. 2 shows the upper means for guiding microwave energy 8 which comprises a upper coaxial tube 26 having an outside surface 28, a first end, a second end 30, an outside diameter, and a longitudinal axis, a substantially rectangular box shaped upper waveguide 32, a magnetron 52, a tubular first upper coax 54, a tubular upper conductor plug 60, a tubular second upper coax 62, a substantially can shaped upper z-neck 70, a tubular upper dielectric disc 84, and a funnel shaped conic support 92.

As shown in FIG. 8, the upper waveguide 32 is a box which has a top plate 34 having an outside surface 36 and a bottom plate 38 having an outside surface 40. The top plate 34 has a first end 42, a second end 44, a first hole 46 between the first end 42 and a center of the top plate and a second hole 48 near the second end 44. The second hole has a diameter smaller than a diameter of the first hole 42. The bottom plate 38 is substantially parallel to the top plate 34 and has a hole 50 of a diameter substantially the same as the diameter of the first hole 46 in the top plate 34. The hole 50 in the bottom plate 38 is oriented in axial alignment with the first hole 46 in the top plate 34. The magnetron 52 is connected to the top plate 34 of the upper waveguide 32 at the second hole 48 so that waves produced by the magnetron 52 are broadcast within the rectangular box shaped upper waveguide. A magnetron identical to one used in a standard household microwave may be successfully used. Magnetrons varying from 300 watts to 3000 watts have been installed; however, a 1400 watt magnetron, such as model 2M121A-53 from Richardson Electronics Ltd., has been used with good results. In a preferred embodiment, the upper wave guide 32 also has a first movable end block 218 and a second movable end block 220. Each movable end block has the characteristic of a tuning short to help tune the microwaves being broadcast.

The first upper coax 54 has a first end 56, a second end 58, an inside surface defining a diameter substantially the same as the diameter of the first hole 46 in the top plate 34 of the upper waveguide 32, and a longitudinal axis. The first end 56 is connected to the outside surface 36 of the top plate 34 so that the longitudinal axis is coaxial with the first hole 46 and the first upper coax 54 is in covering relationship to the first hole 46. A welded connection has proved successful, although other attachment means could be used. The upper conductor plug 60 has a first end, a second end, an outside diameter substantially the same as the inside diameter of the first upper coax 54, an inside surface defining a diameter substantially the same as the outside diameter of the upper coaxial tube 26, and a longitudinal axis. The upper conductor plug 60 is closely received by the second end 58 of the first upper coax 54. In a preferred embodiment, the upper plug may be adjusted up and down within the first coax, thus allowing the conductor plug to function as a tuning short. The first upper coax and upper conductor plug help direct and turn the microwave energy from the upper waveguide to the upper coaxial tube.

The second upper coax 62 has a first end 64, a flange end 66, an inside surface 68 having a diameter substantially the same as the diameter of the hole 50 in the bottom plate 38 of the upper waveguide 32, and a longitudinal axis. The flange end 66 is substantially ring shaped and has a generally cylindrical inside surface coincident with the inside surface 68 of the second upper coax 62. The first end 64 is connected to the outside surface 40 of the bottom plate 38 so that the longitudinal axis is coaxial with the hole 50 and the second upper coax 62 is in covering relationship to the hole 50. A welded connection has proved effective.

FIG. 9 shows the upper z-neck 70 which has a top end 72, a flange end 74, a generally tubular sidewall 76 having an outside surface 78 connecting the top end 72 and the flanged end 74 and an inside surface 80 having a diameter greater than the diameter of the second upper coax 62, and a longitudinal axis. The top end 72 has a hole 82 coaxial with the longitudinal axis. This hole 82 has a diameter substantially the same as the diameter of the inside surface 68 of the second upper coax 62. The flange end 74 is substantially ring shaped and has a generally cylindrical inside surface coincident with the inside surface 80 of the upper z-neck 70. The top end 72 is connected to the flange end 66 of the second upper coax 62. A bolted attachment has proved successful. The flange end 74 is connected to the outside surface 20 of the upper outer shell 4 in covering relationship to the hole 24 in the apex of the upper outer shell 4. Again, a bolted attachment has proved successful. The upper z-neck and second upper coax help to direct the microwave energy towards the upper means for dispersing microwave energy.

The upper dielectric disc 84 has a first end 86, a second end 88, an outside diameter, a longitudinal axis, and an inside surface defining a diameter 90 substantially the same as the outside diameter of the upper coaxial tube 26. The conic support, shown in FIG. 10, has an inside surface defining a diameter substantially the same as the outside diameter of the upper coaxial tube 26, a top surface 94 which has an outside diameter smaller than the outside diameter of the upper dielectric disc 84, a bottom surface 96 which has an outside diameter smaller than the outside diameter of the top surface 94, and a longitudinal axis. The top surface 94 is connected to the second end 88 of the upper dielectric disc 84 by use of an adhesive such as silicon chalk. The upper dielectric disc 84 and the conic support 92 need to have the characteristic of being substantially transparent to microwaves, thus functioning as windows. It has been found that virgin polytetrafluorethylene works well with the type microwaves being broadcast.

The longitudinal axes of the upper shell 4, upper coaxial tube 26, first upper coax 54, upper conductor plug 60, second upper coax 62, upper z-neck 70, dielectric disc 84, and conic support 92 are all coaxial. Further, the upper coaxial tube 26 extends through the upper conductor plug 60, first upper coax 54, upper waveguide 32, second upper coax 62, upper z-neck 70, upper dielectric disc 84 and conic support 92.

The upper coaxial tube, upper waveguide, first upper coax, upper conductor plug, second upper coax, and upper z-neck are made from a microwave friendly material, such as silver, nickel or aluminum. Aluminum is preferred for ease of fabrication and cost.

The upper means for dispersing microwave energy 12, also shown in FIG. 2, comprises a generally ring shaped collar 98, an upper liner 104, a hollow deflection cone 126, and a tubular upper deflector collar 134. The collar, shown in FIG. 11, has a first end 100, a second end 102, an outside diameter, a first generally cylindrical inside surface 302 having a first inside diameter adjacent to the first end 100, a second generally cylindrical inside surface 304 having a second inside diameter which is smaller than the first inside diameter, a first annular shoulder 306 joining the first generally cylindrical surface 302 with the second generally cylindrical 304 surface, a third generally frustoconically shaped inside surface 308 adjacent to the second end and converging from the second end 102 toward a longitudinal axis of the collar 98 at an angle of about 5 degrees, and a second annular shoulder 310 joining the second generally cylindrical surface 304 with the third generally frustoconically shaped inside surface 308. The first inside diameter is substantially the same as the outside diameter of the upper dielectric disc 84 so as to closely receive the upper dielectric disc 84. The second inside diameter is substantially the same as the diameter of the hole 82 in the top end 72 of the upper z-neck 70. The second inside diameter and the frustoconically shaped inside surface 308 are larger than the outside diameter of the conic support 92. The outside diameter of the collar is smaller than the diameter of the inside surface 80 of the upper z-neck 70 so that the upper dielectric disc 84, conic support 92 and collar 98 all nest within the upper z-neck 70. The collar is preferably made from aluminum.

Figure 12:
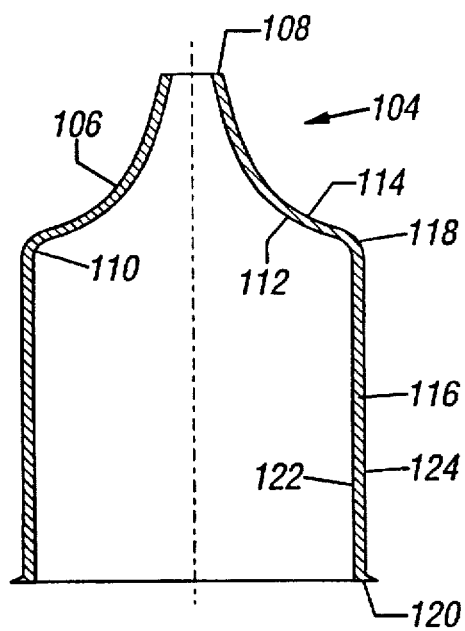
FIG. 12 is a cross-sectional view of the upper inner liner.

FIG. 12 shows the upper liner which has a longitudinal axis and comprises a parabolic shaped bell portion 106 having a first end 108 having an inside diameter, a second end 110 having an inside diameter larger than the inside diameter of the first end 108, an inside surface 112 and an outside surface 114, and a tubular shaped extension portion 116 having a first end 118 connected to the second end 110 of the parabolic shaped bell portion 106, a second flanged end 120, an inside surface 122, and an outside surface 124. The parabolic shape depicted in FIG. 19 has been used with good results. The outside surface 114 of the parabolic shaped bell portion 106 at the first end 108 is connected to the third generally frustoconically shaped inside surface 308 of the collar such that the upper dielectric window is substantially on top of the bell portion in covering relationship to the first end and the conic support is within the bell portion at the first end. The second flanged end 120 of the extension portion 116 nests against the ranged bottom end 22 of the upper outer shell 4. The ranged end is designed to not only provide a pressure seal when the system is clamped together, but to provide an RF energy seal for the system. The outside surfaces 114, 124 of the parabolic shaped bell portion 106 and the tubular shaped extension portion 116 of the upper inner liner 104 are adjacent to the inside surface 18 of the upper outer shell 4. In a preferred embodiment, the upper liner is constructed from aluminum and the parabolic bell shaped portion is formed by spinning. The parabolic shaped bell portion and the extension portion may be made from a single piece, however, it has been found easier to fabricate the portions as separate parts and then weld them together.

Figure 13:
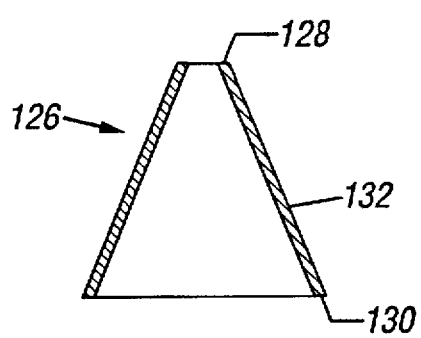
FIG. 13 is a cross-sectional view of the deflection cone.

The upper deflection cone 126, shown in FIG. 13, has a truncated first end 128, a second end 130, a longitudinal axis, and an outside surface 132 converging from the second end 130 towards the first end 128 at an angle between 45 degrees and 55 degrees. The truncated first end 128 has an inside diameter substantially the same as the outside diameter of the upper coaxial tube 26 and the cone is attached to the outside surface 28 of the upper coaxial tube 26 at the truncated first end 128 at a position between the collar 98 and the second end 130 of the deflector cone 126. A welded attachment has proved successful. It is preferred that the cone be placed in position such that the second end 130 and the bottom of the parabolic shaped bell portion are contained in the same plane. The outside surface 132 of the deflection cone 126 is adjacent to the inside surface 112 of the parabolic shaped bell portion 106. The deflection cone, like the upper liner, is preferably fabricated from aluminum.

The upper deflection collar, otherwise known as a "donut" has a first end, a second end, an outside diameter substantially smaller than an inside diameter of the second end 130 of the deflection cone 126, an inside surface having a diameter substantially the same as the outside diameter of the upper coaxial tube 26, and a longitudinal axis. The inside surface is connected to the upper coaxial tube 26 near the second end 30 of the upper coaxial tube 26 such that a plane which contains the second end 130 of the deflection cone 126 passes through the upper deflection collar normal to the longitudinal axis of the upper deflection collar. The upper deflector collar is preferable made from aluminum.

While not wishing to be bound to any theory of operation, it is believed that the microwave energy travels down the upper coaxial tube from the upper means for guiding microwave energy into the upper means for dispersing microwave energy, where it is split into three paths, the first being between the upper liner and the deflection cone. The second path is along the inside surface of the deflection cone and the third path is along the upper coaxial tube. The upper deflection collar acts to redirect energy which stands off the second end of the deflection cone. The waves are redirected into the inside of the deflection cone or to the parabolic shaped bell portion of the upper liner.

The longitudinal axes of the upper outer shell 4, upper coaxial tube 26, collar 98, upper liner 104, deflection cone 126 and upper deflection collar 134 are coaxial. Further, the upper coaxial tube 26 extends through the collar 98, parabolic shaped bell portion 106, deflection cone 126 and upper deflection collar 134.

Figure 3:
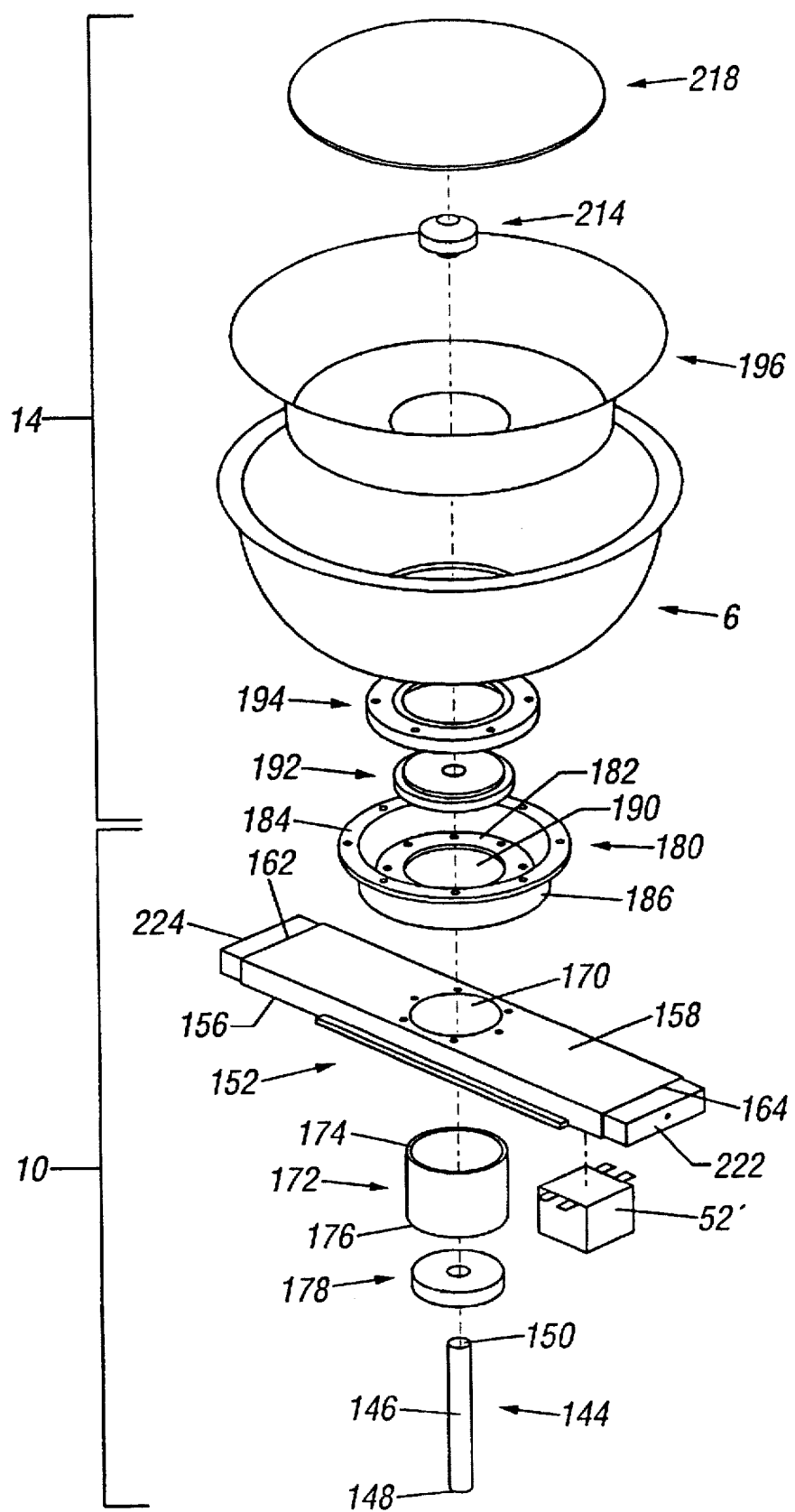
FIG. 3 is an exploded view of the lower sections.
Figure 4:
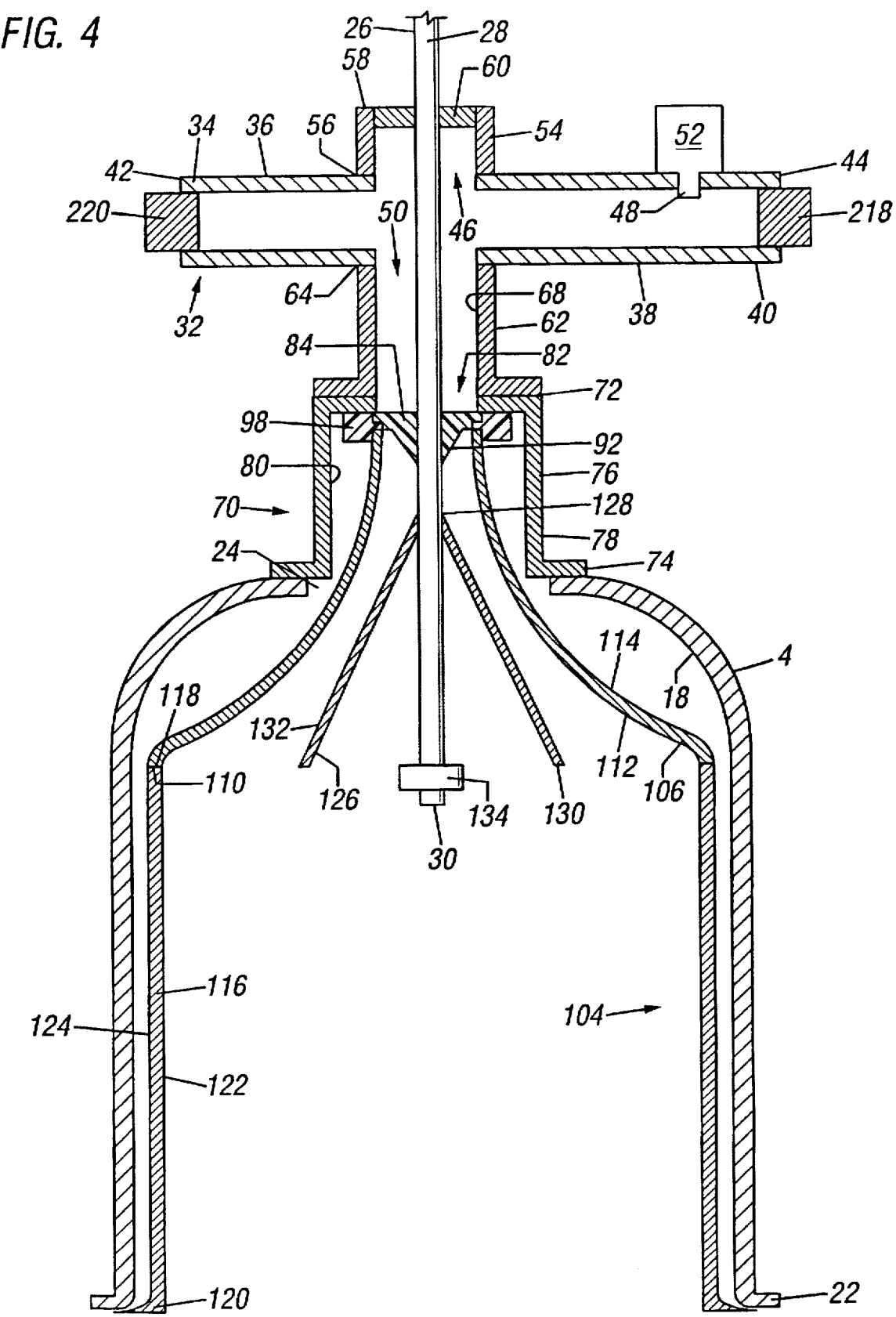
FIG. 4 is a cross-sectional view of the upper sections as assembled.
Figure 5:
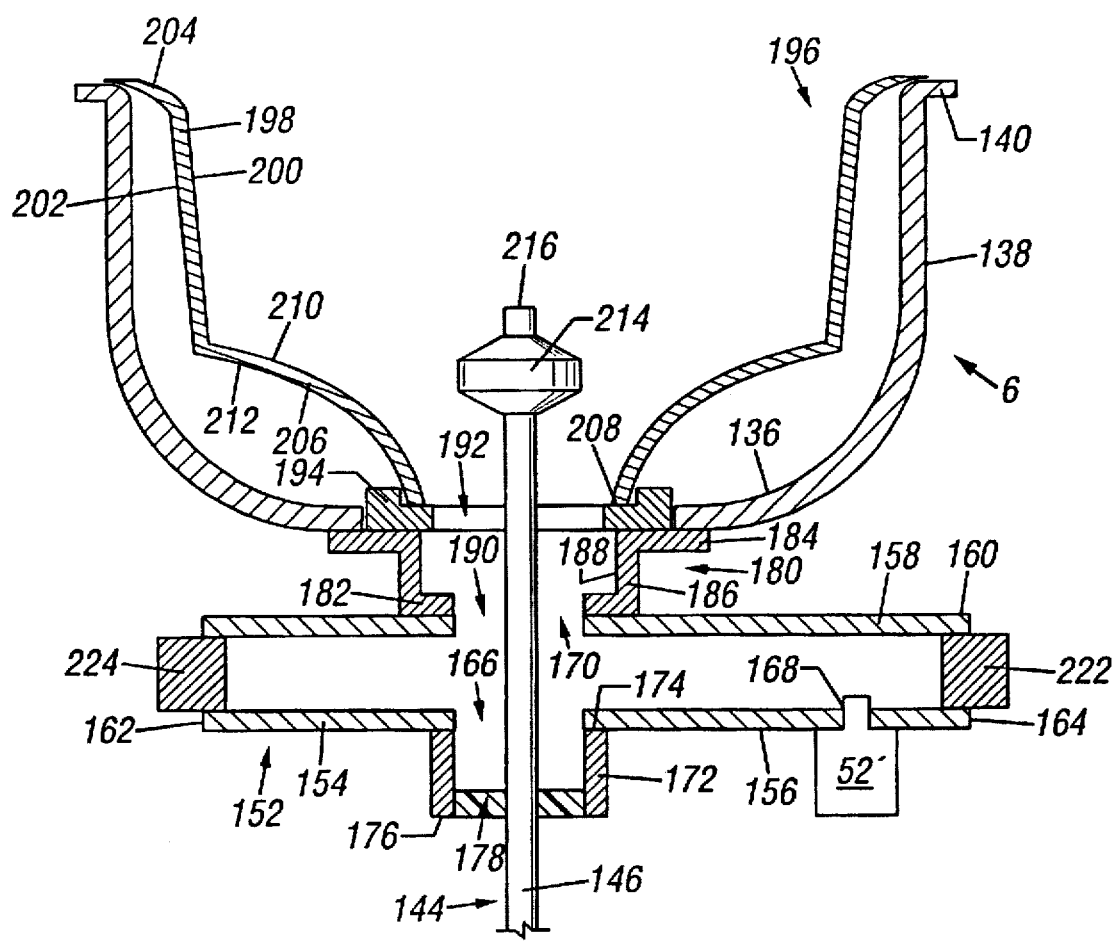
FIG. 5 is a cross-sectional view of the lower sections as assembled.

FIG. 3 shows the lower means for guiding microwave energy 10. Similar to the upper means for guiding microwave energy, the lower means for guiding microwave energy comprises a lower coaxial tube 144 having an outside surface 146, a first end 148, a second end 150, an outside diameter, and a longitudinal axis, a substantially rectangular box shaped lower waveguide 152, a magnetron 52', a tubular lower coax 172, a tubular lower conductor plug 178, a substantially can shaped lower z-neck 180, and a generally tubular lower dielectric disc 192.

The lower waveguide 152, shown in FIG. 8, is identical to that described for the upper waveguide, only upside down. There is a top plate 158 having an outside surface 160 and a bottom plate 154 having an outside surface 156. The bottom plate 154 has a first end 162, a second end 164, a first hole 166 between the first end 162 and a center of the bottom plate and a second hole 168 near the second end 164. The second hole has a diameter smaller than a diameter of the first hole 166. The top plate 158 is substantially parallel to the bottom plate 154 and has a hole 170 of a diameter substantially the same as the diameter of the first hole 166 in the bottom plate 154. This hole 170 in the top plate 158 is in axial alignment with the first hole 166 in the bottom plate 154. A magnetron 52' is connected to the bottom plate 154 of the lower waveguide 152 at the second hole 168 so that waves produced by the magnetron 52' are broadcast within the rectangular box shaped lower waveguide 152. The lower magnetron is similar to the upper magnetron. When energized, the upper and lower magnetrons are set to broadcast at least 120 degrees out of phase with each other. In a preferred embodiment, the lower wave guide 152 also has a first movable end block 222 and a second movable end block 224. Each movable end block functions as a tuning short.

The lower coax 172 has a first end 174, a second end 176, an inside surface defining a diameter substantially the same as the diameter of the first hole 166 in the bottom plate 154 of the lower waveguide 152, and a longitudinal axis. The first end 172 is connected to the outside surface 156 of the bottom plate 154 so that the longitudinal axis is coaxial with the first hole 166 and the lower coax 172 is in covering relationship to the first hole 166. A plate may be attached to the first end to act as a stiffener. If used, the plate must have a hole substantially the same as the inside diameter of the lower coax. A lower conductor plug 178 is used in association with the lower coax. The conductor plug has a first end, a second end, an outside diameter substantially the same as the inside diameter of the lower coax 172, an inside surface defining a diameter substantially the same as the outside diameter of the lower coaxial tube 144, and a longitudinal axis. The lower conductor plug 178 is closely received by the second end 176 of the lower coax 172. In a preferred embodiment, the position of the lower conductor plug is adjustable within the lower coax so that the lower conductor plug functions as a tuning short. The lower coax and lower conductor plug help direct and turn the microwave energy from the lower waveguide to the lower coaxial tube.

Figure 14:
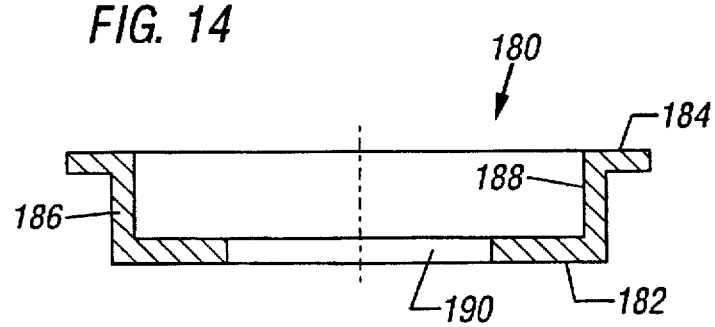
FIG. 14 is a cross-sectional view of the lower z-neck.

FIG. 14 shows the lower z-neck 180 which has a bottom end 182, a flange end 184, a generally tubular sidewall 186 having an outside surface connecting the bottom end 182 and the flanged end 184 and an inside surface 188 having a diameter greater than the diameter of the hole 170 in the top plate 158 of the lower waveguide 152, and a longitudinal axis. The bottom end 182 has a hole 190 coaxial with the longitudinal axis. The hole 190 has a diameter substantially the same as a diameter of the hole 170 in the top plate 158 of the lower waveguide 152. The flange end 184 is substantially frog shaped and has a generally cylindrical inside surface coincident with the inside surface 188 of the lower z-neck 180. The bottom end 182 is connected to the top plate 158 of the lower waveguide 152 so that the hole 190 in the bottom end 182 is coaxial with the hole 170 in the top plate 158 and the bottom end 182 is in covering relationship with the hole 170. The flange end 184 is connected to the outside surface 138 of the lower outer shell 6 in coveting relationship to the hole 142 in the apex of the bell shape of the lower outer shell 6. A plate may be used between the lower z-neck and the lower waveguide to act as a stiffener. If used, the plate must have a hole substantially the same as the hole in the top plate of the waveguide. The lower z-neck helps to direct the microwave energy towards the lower means for dispersing microwave energy.

Figure 15:
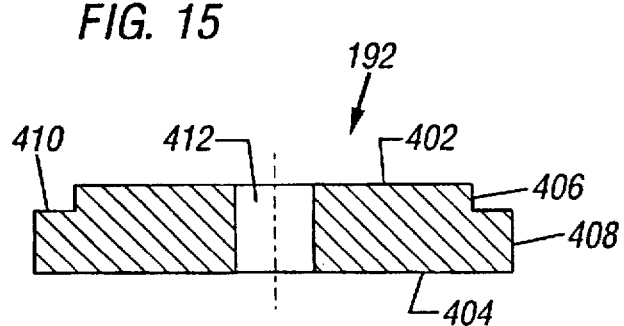
FIG. 15 is a cross-sectional view of the lower dielectric disc.

The lower dielectric disc 192, shown in FIG. 15, has a first end 402, a second end 404, a longitudinal axis, a first outside surface 406 adjacent to the first end 402 and having a first outside diameter, a second outside surface 408 adjacent to the second end 404 and having a second outside diameter which is greater than the first outside diameter, a first annular shoulder 410 joining the first outside surface 406 and the second outside surface 408, and an inside surface defining a diameter substantially the same as the outside diameter of the lower coaxial tube 144. The lower dielectric disc 192 is positioned in the lower z-neck 180 in covering relationship with the hole 190 in the bottom end 182 of the lower z-neck 180. The lower dielectric disc 192 has the characteristic of being substantially transparent to microwaves, thus functioning as a window. It has been found that virgin polytetrafluorethylene functions well as the dielectric material.

The longitudinal axes of the lower outer shell 6, lower coaxial tube 144, lower coax 172, lower conductor plug 178, lower z-neck 180 and lower dielectric disc 192 are coaxial. Further, the lower coaxial tube 144 extends through the lower conductor plug 178, lower coax 172, lower waveguide 152, lower z-neck 180 and lower dielectric disc 192.

The lower waveguide, lower coaxial tube, lower coax, lower conductor plug, and lower z-neck are made from a microwave friendly material, such as silver, nickel or aluminum. Aluminum is preferred for ease of fabrication and cost.

The lower means for dispersing microwave energy is shown in FIG. 3. The system comprises a generally tubular adaptor 194, a lower inner liner 196, and a lower deflector 214. The adaptor 194, shown in FIG. 16, has a first end 502, a second end 504, a first inside surface 506 adjacent to the first end 502 and having a first inside diameter, a second inside surface 508 adjacent to the second end 504 and having a second inside diameter smaller than the first inside diameter, a first annular shoulder 510 joining the first inside surface 506 and the second inside surface 508, a first outside surface 512 adjacent to the first end 502 and having a first outside diameter, a second outside surface 514 adjacent to the second end 504 and having a second outside diameter smaller than the first outside diameter, a second annular shoulder 516 joining the first outside surface 512 and the second outside surface 514, and a longitudinal axis. The first inside diameter is substantially the same as the first outside diameter of the lower dielectric disc 192 so as to closely receive the lower dielectric disc 192. The second inside diameter is substantially the same as the diameter of the hole 190 in the bottom end 182 of the lower z-neck 180. The first outside diameter is smaller than the diameter of the inside surface 188 of the lower z-neck 180. This allows the lower dielectric disc 192 and the adapter 194 to nest within the lower z-neck 180. The adaptor is preferably made from aluminum.

FIG. 17 shows the lower liner 196 which is symmetric about a longitudinal axis and comprises a substantially tubular shaped portion 198 and a parabolic shaped bell portion 206 which is connected to the tubular shaped portion at a point of transition. The tubular portion has an inside surface 200, an outside surface 202, and a ranged end 204. The parabolic shaped bell portion has a first end 208 having an inside diameter smaller than an inside diameter of the tubular shaped portion, an inside surface 210 and an outside surface 212. The parabolic shape depicted in FIG. 19 has been used with good results. It has been found beneficial if the point of transition between the tubular portion and the parabolic shaped bell portion is generally a sharp angle near to 90 degrees. The outside surface 212 of the parabolic shaped bell portion 206 at the first end 208 is closely received by the first inside surface 506 of the adaptor 194. The ranged end 204 of the tubular shaped portion 198 nests against the flanged top end 140 of the lower outer shell 6. As in the upper inner liner, the flanged end is designed to not only provide a pressure seal when the system is clamped together, but to provide an RF energy seal for the system.

The outside surfaces 202, 212 of the tubular portion 198 and the parabolic shaped bell portion 206 of the lower inner liner 196 are adjacent to the inside surface 136 of the lower outer shell 6. In a preferred embodiment, the lower inner liner is fabricated from aluminum and is formed by a spinning process.

The lower deflector 214, shown in FIG. 18, has a first end 602, a second end 604, a first generally frustoconically shaped outside surface 606 adjacent to the first end 602, a second generally frustoconically shaped outside surface 608 adjacent to the second end 604, a third generally cylindrical outside surface 610 connecting the first outside surface 606 and the second outside surface 608, and a longitudinal axis. The first frustoconically shaped outside surface 606 converges away from the first end 602 at an angle of between about 8 degrees and 25 degrees. The second frustoconically shaped outside surface 608 converges away from the second end 604 at an angle between about 8 degrees and 25 degrees, thereby substantially mirroring the first frustoconically shaped outside surface 606. The second end 604 is connected to the second end 150 of the lower coaxial tube 144 such that a common plane passes through the lower deflector and the near 90 degree point of transition between the tubular portion 198 and the parabolic shaped bell portion 206 of the lower inner liner 196. The lower deflector is preferably made from aluminum.

The microwave energy travels up the lower coaxial tube from the lower means for guiding microwave energy into the lower means for dispersing microwave energy, where it is split into two paths, the first being between the liner and the deflector and the second path being along the lower coaxial tube. The lower deflector acts to redirect energy which stands off the near 90 degree point of transition between the tubular portion 198 and the parabolic shaped bell portion 206 of the lower liner. The energy is redirected towards the parabolic shaped bell portion and a central area within the lower liner. A nipple 216 may be added to the second end 604 of the deflector 214 to further tune the microwave energy which stands off the inner liner at the near 90 degree point of transition between the tubular portion 198 and the parabolic shaped bell portion 206. The nipple should be cylindrical with a longitudinal axis coaxial with the longitudinal axis of the deflector 214.

The longitudinal axes of the lower outer shell 6, lower coaxial tube 144, adaptor 194, lower inner liner 196 and deflector 214 are coaxial. Further, the lower coaxial tube 144 extends through the adapter 194, parabolic shaped bell portion 206 of the inner liner 198 and deflector 214.

In a preferred embodiment, the microwave waste sterilizer 2 should also include a reusable plastic waste container, a disc shaped support tray 216 positioned to support the waste container within the microwave waste sterilizer 2, a liner heater, and a means for external control. The support tray 218 needs to have the characteristic of being substantially transparent to microwaves. A disc made from virgin polytetrafluorethylene works well. The liner heater reduces the process time by preheating the metallic parts of the system, thereby offsetting loss of heat generated by the microwaves to the metallic parts of the sterilizer. The means for external control can be any electronic control system, such as a microcomputer.

As stated previously, the flanged ends of the upper and lower outer shells are designed to be held together by a clamp. Preferably, the clamp 16 releasably connects the bottom flanged end 22 of the upper outer shell 4 and the top flanged end 140 of the lower outer shell 6 such that the upper 26 and lower 144 coaxial tubes are aimed at each other. The clamp 16 should also allow the clamped microwave waste sterilizer 2 to maintain an internal pressure between 0.138 MPa (20 psig) and 1.38 MPa (200 psig). It has been found that a split ring clamp that forms to a surface of the flanged end at an angle will provide the greatest amount of holding tension with a minimum of pressure to the clamp. Further, the use of a o-ring in the pressure seal area may be employed to act as both a gasket and a relief valve, preventing the sterilizer from over-pressurizing. The flanged ends of the lower liner can contain a circumferential groove to accept the o-ring. Compressing the o-ring by the clamping process to a compression of about 20 percent has proved satisfactory.

The microwave waste sterilizer can be made to fit into a superstructure which is only slightly larger than a refrigerator. A hydraulic system, such as those available from Tokyo Sintered Metals Corp., Toyko, Japan, can be used with good results to open and close the clamp and to raise and lower the upper portion of the sterilizer. The cylinders may be suspended from the top of the superstructure. The lower portion of the sterilizer can be mounted on a drawer assembly to allow the operator to open the drawer, once the upper portion is raised, and to place or remove the reusable plastic waste container in the lower portion. Any moisture added and condensate formed during the sterilization process can be gathered and recycled as moisture addition for the next cycle. Therefore, an external drain is not necessary.

In another embodiment of the invention, there is provided a method for sterilizing waste materials. The method comprises placing waste materials in a reusable plastic waste container, placing the waste container in a microwave waste sterilizer, clamping the microwave waste sterilizer closed, broadcasting an upper magnetron and a lower magnetron simultaneously so as to generate microwave energy within the microwave waste sterilizer, injecting water into the microwave waste sterilizer, maintaining a predetermined pressure within the microwave waste sterilizer for a predetermined time period, ceasing the generation of microwave energy, venting the microwave waste sterilizer, opening the waste sterilizer, and removing the waste container. In a preferred embodiment of the process, the lower magnetron unit broadcasts at least 120 degrees out of phase from the upper magnetron unit. Also, the water is injected in a pre-determined number of batches. The injected water, along with any condensate, can be trapped and recycled for the next cycle, eliminating the need for an outside drain.

The microwave waste sterilizer 2 comprises a generally bell shaped upper outer shell 4, a generally bowl shaped lower outer shell 6, an upper means for guiding microwave energy 8 connected to the upper outer shell, a lower means for guiding microwave energy 10 connected to the lower outer shell, an upper means for dispersing microwave energy 12 connected to the upper means for generating microwaves, a lower means for dispersing microwave energy 14 connected to the lower means for generating microwaves, and a clamp 16 releasably holding the upper shell and the lower shell together, all substantially as previously described.

In yet another embodiment of the invention, there is provided a method for dispersing microwave energy into a chamber. The method comprises broadcasting microwave energy across a chamber, reflecting the microwave energy from a surface of the chamber, coupling the microwave energy onto a means for coaxial guidance and changing direction of flow to a new direction of flow substantially parallel to the means for coaxial guidance, propagating the microwave energy in the new direction of flow within a means for guiding microwave energy, splitting the microwave energy in a means for dispersing microwave energy, and broadcasting the dispersed microwave energy into a chamber in a flux field of substantially uniform flux. The microwave energy is split into two paths by the means for dispersing microwave energy and the resultant flux field is substantially cone shaped.

Referring to the figures, the chamber used to broadcast microwave energy comprises a substantially rectangular box shaped waveguide 152 and a coax 172. The waveguide 152 has a first side plate 154 having an outside surface 156, a second side plate 158 substantially parallel to the first side plate and having an outside surface 160, a first movable end block 222 substantially normal to the first and second side plates 154,158 and a second movable end block 224 substantially parallel to the first movable side plate 222. The first side plate 154 has a first end 162, a second end 164, a first hole 166 between the first end and a center of the first side plate and a second hole 168 near the second end having a diameter smaller than a diameter of the first hole. The second side plate 158 has a hole 170 of a diameter substantially the same as the diameter of the first hole 166 in the first side plate 154. The hole 170 in the second side plate is oriented in axial alignment with the first hole 166 in the first side plate. The first and second movable end blocks 222,224 each have the characteristic of a tuning short. A magnetron 52 is connected to the first side plate 154 of the waveguide at the second hole 168 so that waves produced by the magnetron are broadcast within the rectangular box shaped waveguide. The tubular coax 172 has a first end 174, a second end 176, an inside surface defining a diameter substantially the same as the diameter of the first hole 166 in the first side plate of the waveguide, and a longitudinal axis. The first end 174 is connected to the outside surface 156 of the first side plate 154 so that the longitudinal axis is coaxial with the first hole 166 and the coax 172 is in covering relationship to the first hole 166. A tubular conductor plug 178 is closely received by the second end 176 of the coax. The conductor plug 178 has a first end, a second end, an outside diameter substantially the same as the inside diameter of the coax, an inside surface defining a diameter substantially the same as an outside diameter of a coaxial tube 144, and a longitudinal axis. The position of the conductor plug 178 is adjustable within the coax 172 and the conductor plug has the characteristic of a tuning short.

The means for coaxial guidance comprises a coaxial tube 144 having an outside surface 146, a first end 148, a second end 150, an outside diameter and a longitudinal axis. The coaxial tube is preferably made from aluminum.

The means for guiding microwave energy comprises a substantially can shaped z-neck 180 and a generally tubular dielectric disc 192. The z-neck 180 has a first end 182, a flange end 184, a generally tubular sidewall 186 having an outside surface connecting the first end 182 and the ranged end 184 and an inside surface 188 having a diameter greater than the diameter of the hole 170 in the second side plate 158 of the waveguide, and a longitudinal axis. The first end 182 has a hole 190 coaxial with the longitudinal axis and having a diameter substantially the same as a diameter of the hole 170 in the second side plate 158 of the waveguide. This first end 182 is connected to the second side plate 158 of the waveguide so that the hole 190 in the first end 182 is coaxial with the hole 170 in the second side plate and the first end 182 is in covering relationship with the hole 170. The flange end 184 is substantially ring shaped and has a generally cylindrical inside surface coincident with the inside surface 188 of the z-neck. The z-neck is preferably made from aluminum. The dielectric disc 192 has a first end 402, a second end 404, a longitudinal axis, a first outside surface 406 adjacent to the first end 402 and having a first outside diameter, a second outside surface 408 adjacent to the second end 404 and having a second outside diameter which is greater than the first outside diameter, a first annular shoulder 410 joining the first outside surface 406 and the second outside surface 408, and an inside surface defining a diameter substantially the same as the outside diameter of the coaxial tube 144. The dielectric disc 192 is positioned in the z-neck 180 in coveting relationship with the hole 190 in the first end 182 of the z-neck. The dielectric disc has the characteristic of being substantially transparent to microwaves. It has been found that virgin polytetrafluorethylene works well for the type microwaves broadcast.

The means for dispersing microwave energy comprises a generally tubular adaptor 194, a generally bowl shaped outer shell 6, an inner liner 196 and a deflector 214. The adaptor 194 has a first end 502, a second end 504, a first inside surface 506 adjacent to the first end 502 and having a first inside diameter, a second inside surface 508 adjacent to the second end 504 and having a second inside diameter smaller than the first inside diameter, a first annular shoulder 510 joining the first inside surface 506 and the second inside surface 508, a first outside surface 512 adjacent to the first end 502 and having a first outside diameter, a second outside surface 514 adjacent to the second end 504 and having a second outside diameter smaller than the first outside diameter, a second annular shoulder 516 joining the first outside surface 512 and the second outside surface 514, and a longitudinal axis. The first inside diameter is substantially the same as the first outside diameter of the dielectric disc 192 so as to closely receive the dielectric disc. The second inside diameter is substantially the same as the diameter of the hole 190 in the first end 182 of the z-neck 180 and the first outside diameter is smaller than the diameter of the inside surface 188 of the z-neck 180 such that the dielectric disc 192 and the adapter 194 nest within the z-neck 180. The adaptor is preferably made from aluminum.

The outer shell 6 has an inside surface 136, an outside surface 138, a longitudinal axis and a hole 142 at an apex of the bowl shape. The outside surface 138 is connected to the flange end 184 of the z-neck 180 so that the z-neck is in covering relationship to the hole 142 in the apex of the bell shape of the outer shell.

The inner liner 196 has a longitudinal axis and two portions, namely a substantially tubular shaped portion 198 having an inside surface 200 and an outside surface 202, and a parabolic shaped bell portion 206 connected to the tubular shaped portion 198 at a point of transition. The parabolic shaped portion 206 has a first end 208 which has an inside diameter smaller than an inside diameter of the tubular shaped portion 198, an inside surface 210 and an outside surface 212. The inner liner 196 is connected to the adaptor 194 at the first end 208 of the parabolic shaped bell portion such that the outside surface 212 at the first end 208 is closely received by the first inside surface 506 of the adaptor 194. The outside surfaces 202, 212 of the tubular shaped portion 198 and the parabolic shaped bell portion 206 of the inner liner are adjacent to the inside surface 136 of the outer shell 6. In a preferred embodiment, the liner is constructed from aluminum and is formed by spinning.

The deflector has a first end 602, a second end 604, a first generally frustoconically shaped outside surface 606 adjacent to the first end 602, a second generally frustoconically shaped outside surface 608 adjacent to the second end 604, a third generally cylindrical outside surface 610 connecting the first outside surface 606 and the second outside surface 608, and a longitudinal axis. The first frustoconically shaped outside surface 606 converges away from the first end 602 at an angle of between about 8 degrees and 25 degrees. The second frustoconically shaped outside surface 608, which mirrors the first frustoconically shaped surface, converges away from the second end 604 at an angle between about 8 degrees and 25 degrees. The second end 604 is connected to the second end 150 of the coaxial tube 144 such that a common plane passes through the lower deflector and the near 90 degree point of transition between the tubular portion 198 and the parabolic shaped bell portion 206 of the lower inner liner 196. The deflector is preferably made from aluminum.

The longitudinal axes of the outer shell, coaxial tube, coax, conductor plug, z-neck, lower dielectric disc, adaptor, inner liner and deflector are coaxial. Also, the coaxial tube extends through the conductor plug, coax, waveguide, z-neck, lower dielectric disc, adapter, parabolic shaped bell portion of the inner liner and deflector.

While not wishing to be bound to any theory of operation, it is believed that the microwave energy is split along at least two paths within the means for dispersing microwave energy. The first path is formed by the coaxial tube. The second path is formed by the inside surfaces of the tubular shaped portion and the parabolic shaped bell portion of the inner liner. The portion of energy that follows the coaxial tube travels down the coaxial tube to the deflector. The energy traveling along the inside surface of the parabolic shaped bell portion reaches the point of transition between the parabolic shaped bell section and the tubular section and changes direction. Much of this energy is directed toward the deflector. A portion of the energy which reaches the deflector is reflected back towards the inner liner, eventually returning to the deflector. Other energy is dispersed from the deflector into a solid cone shaped flux field. The flux field is substantially uniform, thus eliminating cold spots seen when the microwave energy is narrowly focused. A nipple 216 may be added to the second end 604 of the deflector 214 to further tune the microwave energy which stands off the inner liner at the near 90 degree point of transition between the tubular portion 198 and the parabolic shaped bell portion 206. The nipple should be cylindrical with a longitudinal axis coaxial with the longitudinal axis of the deflector 214.

The foregoing provides a description of the preferred embodiments, however, it should be noted that numerous structural changes and modifications may be made without departing from the spirit of the invention.

We claim:

1. A microwave waste sterilizer comprising:

a upper outer shell;

a lower outer shell;

an upper means for guiding microwave energy connected to said upper outer shell;

a lower means for guiding microwave energy connected to said lower outer shell;

an upper means for dispersing microwave energy connected to said upper means for guiding microwave energy;

a lower means for dispersing microwave energy connected to said lower means for guiding microwave energy; and a clamp releasably holding said upper outer shell and said lower outer shell together wherein the upper outer shell is generally bell shaped having an inside surface, an outside surface, a flanged bottom end, and a longitudinal axis, said outer shell further defining a hole substantially at the apex of the bell shape, said hole coaxial with the longitudinal axis, wherein the upper means for guiding microwave energy comprises:

a upper coaxial tube having an outside surface, a first end, a second end, an outside diameter, and a longitudinal axis;

a substantially rectangular box shaped upper waveguide having a top plate having an outside surface, a first end and a second end, and a bottom plate having an outside surface, said top plate further defining a first hole between the first end and a center of said top plate and a second hole near the second end having a diameter smaller than a diameter of the first hole, said bottom plate being substantially parallel to said top plate and defining a hole of a diameter substantially the same as the diameter of the first hole in said top plate, said hole in said bottom plate further oriented in axial alignment with the first hole in said top plate;

a magnetron connected to the top plate of the upper waveguide at the second hole so that waves produced by said magnetron are broadcast within said rectangular box shaped upper waveguide;

a tubular first upper coax having a first end, a second end, an inside surface defining a diameter substantially the same as the diameter of the first hole in the top plate of said upper waveguide, and a longitudinal axis, said first end connected to the outside surface of said top plate so that the longitudinal axis is coaxial with the first hole in said top plate and the first upper coax is in covering relationship to the first hole;

a tubular upper conductor plug having a first end, a second end, an outside diameter substantially the same as the inside diameter of said first upper coax, an inside surface defining a diameter substantially the same as the outside diameter of said upper coaxial tube, and a longitudinal axis, said upper conductor plug closely received by the second end of said first upper coax;

a tubular second upper coax having a first end, a flange end, an inside surface having a diameter substantially the same as the diameter of the hole in the bottom plate of said waveguide, and a longitudinal axis, said flange end being substantially ring shaped and having a generally cylindrical inside surface coincident with the inside surface of said second upper coax, said first end connected to the outside surface of said bottom plate so that the longitudinal axis is coaxial with the hole in said bottom plate and the second upper coax is in covering relationship to the hole in said bottom plate;

a substantially can shaped upper z-neck having a top end, a flange end, a longitudinal axis, and a generally tubular sidewall having an outside surface connecting the top end and the flanged end and an inside surface defining a diameter greater than the diameter of said second upper coax, said top end defining a hole coaxial with the longitudinal axis and having a diameter substantially the same as the diameter of the inside surface of said second upper coax, said flange end being substantially ring shaped and having a generally cylindrical inside surface coincident with the inside surface of said upper z-neck, said top end connected to the flange end of said second upper coax, said flange end connected to the outside surface of said upper outer shell in covering relationship to the hole in the apex of said upper outer shell;

a tubular upper dielectric disc having a first end, a second end, an outside diameter, a longitudinal axis, and an inside surface defining a diameter substantially the same as the outside diameter of said upper coaxial tube, said upper dielectric disc having the characteristic of being substantially transparent to microwaves; and a funnel shaped conic support having an inside surface defining a diameter substantially the same as the outside diameter of said upper coaxial tube, a top surface having an outside diameter smaller than the outside diameter of said upper dielectric disc, a bottom surface having an outside diameter smaller than the outside diameter of said top surface, and a longitudinal axis, said top surface connected to the second end of said upper dielectric disc, said conic support having the characteristic of being substantially transparent to microwaves;

wherein the longitudinal axes of said upper shell, upper coaxial tube, first upper coax, upper conductor plug, second upper coax, upper z-neck, dielectric disc, and conic support are coaxial; and wherein said upper coaxial tube extends through said upper conductor plug, first upper coax, upper waveguide, second upper coax, upper z-neck, upper dielectric disc and conic support.

2. The microwave waste sterilizer of claim 1 wherein the upper means for dispersing microwave energy comprises:

a generally ring shaped collar having a first end, a second end, an outside diameter, a first generally cylindrical inside surface defining a first inside diameter adjacent to the first end, a second generally cylindrical inside surface defining a second inside diameter which is smaller than the first inside diameter, a first annular shoulder joining the first generally cylindrical surface with the second generally cylindrical surface, a third generally frustoconically shaped inside surface adjacent to the second end, said frustoconically shaped inside surface converging from the second end toward a longitudinal axis of the collar at an angle of about 5 degrees, and a second annular shoulder joining the second generally cylindrical surface with the third generally frustoconically shaped inside surface, said first inside diameter substantially the same as the outside diameter of said upper dielectric disc so as to closely receive said upper dielectric disc, said second inside diameter substantially the same as the diameter of the hole in the top end of said upper z-neck, said second inside diameter and said frustoconically shaped inside surface larger than the outside diameter of said conic support, said outside diameter smaller than the diameter of the inside surface of said upper z-neck such that the upper dielectric disc, conic support and collar all nest within said z-neck;

an upper liner having a longitudinal axis, said upper liner comprising
 a parabolic shaped bell portion having a first end defining an inside diameter, a second end defining an inside diameter larger than the inside diameter of said first end, an inside surface and an outside surface, and
 a tubular shaped extension portion having a first end connected to the second end of said parabolic shaped portion, a second flanged end, an inside surface, and an outside surface,
 wherein the outside surface of said parabolic shaped bell portion at the first end is connected to the third generally frustoconically shaped inside surface of said collar; and
 wherein the second flanged end of the extension portion nests against the flanged bottom end of said upper outer shell;

a hollow deflection cone having a truncated first end, a second end, a longitudinal axis, and an outside surface converging from the second end towards the first end at an angle between 45 degrees and 55 degrees, said truncated first end defining an inside diameter substantially the same as the outside diameter of said upper coaxial tube, said truncated first end connected to the outside surface of said upper coaxial tube at a position between said collar and the second end of said deflection cone; and a tubular upper deflection collar having a first end, a second end, an outside diameter substantially smaller than an inside diameter of the second end of said deflection cone, an inside surface defining a diameter substantially the same as the outside diameter of said upper coaxial tube, and a longitudinal axis, said inside surface connected to the upper coaxial tube near the second end of said upper coaxial tube such that a plane normal to the longitudinal axis of said upper deflection collar is coplanar with a plane containing the second end of said deflection cone;

wherein the outside surfaces of said parabolic shaped bell portion and said tubular shaped extension portion of said upper inner liner are adjacent to the inside surface of said upper outer shell;

wherein the outside surface of said deflection cone is adjacent to the inside surface of said parabolic shaped bell portion;

wherein the longitudinal axes of said upper outer shell, upper coaxial tube, collar, upper liner, deflection cone and upper deflection collar are coaxial; and wherein said upper coaxial tube extends through said collar, parabolic shaped portion, deflection cone and upper deflection collar.

3. The microwave sterilizer of claim 2 wherein the lower outer shell is generally bowl shaped having an inside surface, an outside surface, a flanged top end, and a longitudinal axis, said lower outer shell further defining a hole at an apex of the bowl shape, said hole coaxial with the longitudinal axis.

4. The microwave waste sterilizer of claim 3 wherein the lower means for guiding microwave energy comprises:

a lower coaxial tube having an outside surface, a first end, a second end, an outside diameter, and a longitudinal axis;

a substantially rectangular box shaped lower waveguide having a top plate having an outside surface and a bottom plate having an outside surface, a first end and a second end, said bottom plate defining a first hole between the first end and a center of said bottom plate and a second hole near the second end having a diameter smaller than a diameter of the first hole, said top plate being substantially parallel to said bottom plate and defining a hole of a diameter substantially the same as the diameter of the first hole in said bottom plate, said hole in said top plate further oriented in axial alignment with the first hole in said bottom plate;

a magnetron connected to the bottom plate of the lower waveguide at the second hole so that waves produced by said magnetron are broadcast within said rectangular box shaped lower waveguide;

a tubular lower coax having a first end, a second end, an inside surface defining a diameter substantially the same as the diameter of the first hole in the bottom plate of said lower waveguide, and a longitudinal axis, said first end connected to the outside surface of said bottom plate so that the longitudinal axis is coaxial with the first hole in said bottom plate and the lower coax is in covering relationship to the first hole in the bottom plate;

a tubular lower conductor plug having a first end, a second end, an outside diameter substantially the same as the inside diameter of said lower coax, an inside surface defining a diameter substantially the same as the outside diameter of said lower coaxial tube, and a longitudinal axis, said lower conductor plug closely received by the second end of said lower coax;

a substantially can shaped lower z-neck having a bottom end, a flange end, a longitudinal axis, and a generally tubular sidewall having an outside surface connecting the bottom end and the flanged end and an inside surface defining a diameter greater than the diameter of the hole in the top plate of said lower waveguide, said bottom end defining a hole coaxial with the longitudinal axis and having a diameter substantially the same as a diameter of the hole in said top plate of said lower waveguide, said flange end being substantially ring shaped and having a generally cylindrical inside surface coincident with the inside surface of said lower z-neck, said bottom end connected to the top plate of said lower waveguide so that the hole in the bottom end is coaxial with the hole in said top plate and said bottom end is in covering relationship with the hole in said top plate, said flange end connected to the outside surface of said lower outer shell in covering relationship to the hole in the apex of the bell shape of said lower outer shell; and a generally tubular lower dielectric disc having a first end, a second end, a longitudinal axis, a first outside surface adjacent to the first end and defining a first outside diameter, a second outside surface adjacent to the second end and defining a second outside diameter which is greater than the first outside diameter, a first annular shoulder joining the first outside surface and the second outside surface, and an inside surface defining a diameter substantially the same as the outside diameter of said lower coaxial tube, said lower dielectric disc having the characteristic of being substantially transparent to microwaves, said lower dielectric disc positioned in said lower z-neck in covering relationship with the hole in the bottom end of said lower z-neck;

wherein the longitudinal axes of said lower outer shell, lower coaxial tube, lower coax, lower conductor plug, lower z-neck and lower dielectric disc are coaxial; and wherein said lower coaxial tube extends through said lower conductor plug, lower coax, lower waveguide, lower z-neck and lower dielectric disc.

5. The microwave waste sterilizer of claim 4 wherein the lower means for dispersing microwave energy comprises:

a generally tubular adaptor having a first end, a second end, a first inside surface adjacent to the first end and defining a first inside diameter, a second inside surface adjacent to the second end and defining a second inside diameter smaller than the first inside diameter, a first annular shoulder joining the first inside surface and the second inside surface, a first outside surface adjacent to the first end and defining a first outside diameter, a second outside surface adjacent to the second end and defining a second outside diameter smaller than the first outside diameter, a second annular shoulder joining the first outside surface and the second outside surface, and a longitudinal axis, said first inside diameter substantially the same as the first outside diameter of said lower dielectric disc so as to closely receive said lower dielectric disc, said second inside diameter substantially the same as the diameter of the hole in the bottom end of said lower z-neck, said first outside diameter smaller than the diameter of the inside surface of said lower z-neck such that the lower dielectric disc and the adapter nest within said lower z-neck;

a lower inner liner having a longitudinal axis comprising
a substantially tubular shaped portion having an inside surface, an outside surface, and a first flanged end,
a parabolic shaped bell portion connected to the tubular shaped portion at a point of transition and having a first end defining an inside diameter smaller than an inside diameter of said tubular shaped portion, an inside surface and an outside surface,
wherein the outside surface of said parabolic shaped bell portion at the first end is closely received by the first inside surface of said adaptor; and
wherein the flanged end of the tubular shaped portion nests against the flanged top end of said lower outer shell; and a lower deflector having a first end, a second end, a first generally frustoconically shaped outside surface adjacent to the first end, a second generally frustoconically shaped outside surface adjacent to the second end, a third generally cylindrical outside surface connecting the first outside surface and the second outside surface, and a longitudinal axis, said first frustoconically shaped outside surface converging away from the first end at an angle of between about 8 degrees and 25 degrees, said second frustoconically shaped outside surface converging away from the second end at an angle between about 8 degrees and 25 degrees, said second frustoconically shaped outside surface substantially mirroring said first frustoconically shaped outside surface, said second end connected to the second end of said lower coaxial tube;

wherein the outside surfaces of said tubular shaped portion and said parabolic shaped bell portion of said inner liner are adjacent to the inside surface of said lower outer shell;

wherein the longitudinal axes of said lower outer shell, lower coaxial tube, adaptor, lower inner liner and deflector are coaxial; and wherein said lower coaxial tube extends through said adapter, parabolic shaped bell portion of said inner liner and deflector.

6. The microwave waste sterilizer of claim 5 further comprising:

a reusable plastic waste container;

a disc shaped support tray positioned to support said waste container within said microwave waste sterilizer, said support tray having the characteristic of being substantially transparent to microwaves; and a means for external control.

7. The microwave waste sterilizer of claim 6 wherein said upper wave guide has a first movable end block and a second movable end block, each said movable end block having the characteristic of a tuning short;

said lower wave guide has a first movable end block and a second movable end block, each said movable end block having the characteristic of a tuning short;

the position of said upper conductor plug is adjustable within said first upper coax and said upper conductor plug has the characteristic of a tuning short; and the position of said lower conductor plug is adjustable within said lower coax and said lower conductor plug has the characteristic of a tuning short.

8. The microwave waste sterilizer of claim 7 wherein said clamp releasably connects the bottom flanged end of said upper outer shell and the top flanged end of said lower outer shell such that the upper and lower coaxial tubes are aimed at each other and the longitudinal axis of said upper coaxial tube coincides with the longitudinal axis of said lower coaxial tube, said clamp further allowing the clamped microwave waste sterilizer to maintain an internal pressure between 0.138 MPa (20 psig) and 1.38 MPa (200 psig).

9. The microwave waste sterilizer of claim 8 wherein the magnetron in the upper waveguide and the magnetron in the lower waveguide broadcast simultaneously and the lower magnetron is at least 120 degrees out of phase from the upper magnetron.

10. The microwave waste sterilizer of claim 9 further comprising a liner heater.

11. The microwave waste sterilizer of claim 9 wherein the upper dielectric disc, conic support, lower dielectric disc, and support tray comprise virgin polytetrafluorethylene.

12. The microwave waste sterilizer of claim 9 wherein the upper inner liner, lower inner liner, and deflection cone comprise aluminum and wherein the parabolic bell shapes of the upper liner and lower liner are formed by spinning.

13. A method for sterilizing waste materials, said method comprising:

placing waste materials in a reusable plastic waste container;

placing the waste container in a microwave waste sterilizer, said microwave waste sterilizer comprising
- a generally bell shaped upper outer shell having an inside surface, an outside surface, a flanged bottom end, and a longitudinal axis, said upper outer shell further defining a hole substantially at the apex of the bell shape, said hole coaxial with the longitudinal axis,
- a generally bowl shaped lower outer shell having an inside surface, an outside surface, a flanged top end, and a longitudinal axis, said lower outer shell further defining a hole at a apex of the bowl shape, said hole coaxial with the longitudinal axis,
- an upper means for guiding microwave energy connected to said upper outer shell,
- a lower means for guiding microwave energy connected to said lower outer shell,
- an upper means for dispersing microwave energy connected to said upper means for guiding microwave energy,
- a lower means for dispersing microwave energy connected to said lower means for guiding microwave energy, and
- a clamp releasably holding said upper shell and said lower shell together; clamping the upper outer shell and the lower outer shell together;

broadcasting an upper magnetron and a lower magnetron simultaneously so as to generate microwave energy within the microwave waste sterilizer;

injecting water into said microwave waste sterilizer;

maintaining a predetermined pressure within said microwave waste sterilizer for a predetermined time period;

ceasing the generation of microwave energy;

venting said microwave waste sterilizer;

opening said waste sterilizer; and removing said waste container.

14. The method for sterilizing waste materials of claim 13 wherein the lower magnetron unit is broadcasting at least 120 degrees out of phase from the upper magnetron unit.

15. The method for sterilizing waste materials of claim 14 wherein the upper means for guiding microwave energy comprises:

a upper coaxial tube having an outside surface, a first end, a second end, an outside diameter, and a longitudinal axis;

a substantially rectangular box shaped upper waveguide having a top plate having an outside surface, a first end and a second end, and a bottom plate having an outside surface, said top plate defining a first hole between the first end and a center of said top plate and a second hole near the second end having a diameter smaller than a diameter of the first hole, said bottom plate being substantially parallel to said top plate and defining a hole of a diameter substantially the same as the diameter of the first hole in said top plate, said hole in said bottom plate further oriented in axial alignment with the first hole in said top plate;

a magnetron connected to the top plate of the upper waveguide at the second hole so that waves produced by said magnetron are broadcast within said rectangular box shaped upper waveguide;

a tubular first upper coax having a first end, a second end, an inside diameter substantially the same as the diameter of the first hole in the top plate of said upper waveguide, and a longitudinal axis, said first end connected to the outside surface of said top plate so that the longitudinal axis is coaxial with the first hole in said top plate and the first upper coax is in covering relationship to the first hole in said top plate;

a tubular upper conductor plug having a first end, a second end, an outside diameter substantially the same as the inside diameter of said first upper coax, an inside diameter substantially the same as the outside diameter of said upper coaxial tube, and a longitudinal axis, said upper conductor plug closely received by the second end of said first upper coax;

a tubular second upper coax having a first end, a flange end, an inside surface defining a diameter substantially the same as the diameter of the hole in the bottom plate of said waveguide, and a longitudinal axis, said flange end being substantially ring shaped and having a generally cylindrical inside surface coincident with the inside surface of said second upper coax, said first end connected to the outside surface of said bottom plate so that the longitudinal axis is coaxial with the hole in said bottom plate and the second upper coax is in covering relationship to the hole in said bottom plate;

a substantially can shaped upper z-neck having a top end, a flange end, a longitudinal axis, and a generally tubular sidewall having an outside surface connecting the top end and the flanged end and an inside surface defining a diameter greater than the diameter of said second upper coax, said top end defining a hole coaxial with the longitudinal axis and having a diameter substantially the same as the diameter of the inside surface of said second upper coax, said flange end being substantially ring shaped and having a generally cylindrical inside surface coincident with the inside surface of said upper z-neck, said top end connected to the flange end of said second upper coax, said flange end connected to the outside surface of said upper outer shell in covering relationship to the hole in the apex of said upper outer shell;

a tubular upper dielectric disc having a first end, a second end, an outside diameter, a longitudinal axis, and an inside surface defining a diameter substantially the same as the outside diameter of said upper coaxial tube, said upper dielectric disc having the characteristic of being substantially transparent to microwaves; and a funnel shaped conic support defining an inside diameter substantially the same as the outside diameter of said upper coaxial tube, a top surface defining an outside diameter smaller than the outside diameter of said upper dielectric disc, a bottom surface defining an outside diameter smaller than the outside diameter of said top surface, and a longitudinal axis, said top surface connected to the second end of said upper dielectric disc, said conic support having the characteristic of being substantially transparent to microwaves;

wherein the longitudinal axes of said upper shell, upper coaxial tube, first upper coax, upper conductor plug, second upper coax, upper z-neck, dielectric disc, and conic support are coaxial; and wherein said upper coaxial tube extends through said upper conductor plug, first upper coax, upper waveguide, second upper coax, upper z-neck, upper dielectric disc and conic support.

16. The method for sterilizing waste materials of claim 15 wherein the upper means for dispersing microwave energy comprises:

a generally ring shaped collar having a first end, a second end, an outside diameter, a first generally cylindrical inside surface defining a first inside diameter adjacent to the first end, a second generally cylindrical inside surface defining a second inside diameter which is smaller than the first inside diameter, a first annular shoulder joining the first generally cylindrical surface with the second generally cylindrical surface, a third generally frustoconically shaped inside surface adjacent to the second end, said frustoconically shaped inside surface converging from the second end toward a longitudinal axis of the collar at an angle of about 5 degrees, and a second annular shoulder joining the second generally cylindrical surface with the third generally frustoconically shaped inside surface, said first inside diameter substantially the same as the outside diameter of said upper dielectric disc so as to closely receive said upper dielectric disc, said second inside diameter substantially the same as the diameter of the hole in the top end of said upper z-neck, said second inside diameter and said frustoconically shaped inside surface larger than the outside diameter of said conic support, said outside diameter smaller than the diameter of the inside surface of said upper z-neck such that the upper dielectric disc, conic support and collar all nest within said z-neck;

an upper liner having a longitudinal axis, said upper liner comprising
 a parabolic shaped bell portion having a first end defining an inside diameter, a second end defining an inside diameter larger than the inside diameter of said first end, an inside surface and an outside surface, and
 a tubular shaped extension portion having a first end connected to the second end of said parabolic shaped portion, a second flanged end, an inside surface, and an outside surface,
 wherein the outside surface of said parabolic shaped bell portion at the first end is connected to the third generally frustoconically shaped inside surface of said collar; and
 wherein the second flanged end of the extension portion nests against the flanged bottom end of said upper outer shell;

a hollow deflection cone having a truncated first end, a second end, a longitudinal axis, and an outside surface converging from the second end towards the first end at an angle between 45 degrees and 55 degrees, said truncated first end defining an inside diameter substantially the same as the outside diameter of said upper coaxial tube, said truncated first end connected to the outside surface of said upper coaxial tube at a position between said collar and the second end of said deflection cone; and a tubular upper deflection collar having a first end, a second end, an outside diameter substantially smaller than an inside diameter of the second end of said deflection cone, an inside surface defining a diameter substantially the same as the outside diameter of said upper coaxial tube, and a longitudinal axis, said inside surface connected to the upper coaxial tube near the second end of said upper coaxial tube such that a plane normal to the longitudinal axis of said upper deflection collar is coplanar with a plane containing the second end of said deflection cone;

wherein the outside surfaces of said parabolic shaped bell portion and said tubular shaped extension portion of said upper inner liner are adjacent to the inside surface of said upper outer shell;

wherein the outside surface of said deflection cone is adjacent to the inside surface of said parabolic shaped bell portion;

wherein the longitudinal axes of said upper outer shell, upper coaxial tube, collar, upper liner, deflection cone and upper deflection collar are coaxial; and wherein said upper coaxial tube extends through said collar, parabolic shaped portion, deflection cone and upper deflection collar.

17. The method for sterilizing waste materials of claim 16 wherein the lower means for guiding microwave energy comprises:

a lower coaxial tube having an outside surface, a first end, a second end, an outside diameter, and a longitudinal axis;

a substantially rectangular box shaped lower waveguide having a top plate having an outside surface and a bottom plate having an outside surface, a first end and a second end, said bottom plate defining a first hole between the first end and a center of said bottom plate and a second hole near the second end having a diameter smaller than a diameter of the first hole, said top plate being substantially parallel to said bottom plate and defining a hole of a diameter substantially the same as the diameter of the first hole in said bottom plate, said hole in said top plate further oriented in axial alignment with the first hole in said bottom plate;

a magnetron connected to the bottom plate of the lower waveguide at the second hole so that waves produced by said magnetron are broadcast within said rectangular box shaped lower waveguide;

a tubular lower coax having a first end, a second end, an inside surface defining a diameter substantially the same as the diameter of the first hole in the bottom plate of said lower waveguide, and a longitudinal axis, said first end connected to the outside surface of said bottom plate so that the longitudinal axis is coaxial with the first hole and the lower coax is in covering relationship to the first hole;

a tubular lower conductor plug having a first end, a second end, an outside diameter substantially the same as the inside diameter of said lower coax, an inside surface defining a diameter substantially the same as the outside diameter of said lower coaxial tube, and a longitudinal axis, said lower conductor plug closely received by the second end of said lower coax;

a substantially can shaped lower z-neck having a bottom end, a flange end, a longitudinal axis, and a generally tubular sidewall having an outside surface connecting the bottom end and the flanged end and an inside surface defining a diameter greater than the diameter of the hole in the top plate of said lower waveguide, said bottom end defining a hole coaxial with the longitudinal axis and having a diameter substantially the same as a diameter of the hole in said top plate of said lower waveguide, said flange end being substantially ring shaped and having a generally cylindrical inside surface coincident with the inside surface of said lower z-neck, said bottom end connected to the top plate of said lower waveguide so that the hole in said bottom end is coaxial with the hole in said top plate and said bottom end is in covering relationship with the hole in said top plate, said flange end connected to the outside surface of said lower outer shell in covering relationship to the hole in the apex of the bell shape of said lower outer shell; and a generally tubular lower dielectric disc having a first end, a second end, a longitudinal axis, a first outside surface adjacent to the first end and defining a first outside diameter, a second outside surface adjacent to the second end and defining a second outside diameter which is greater than the first outside diameter, a first annular shoulder joining the first outside surface and the second outside surface, and an inside surface defining a diameter substantially the same as the outside diameter of said lower coaxial tube, said lower dielectric disc having the characteristic of being substantially transparent to microwaves, said lower dielectric disc positioned in said lower z-neck in covering relationship with the hole in the bottom end of said lower z-neck;

wherein the longitudinal axes of said lower outer shell, lower coaxial tube, lower coax, lower conductor plug, lower z-neck and lower dielectric disc are coaxial; and wherein said coaxial tube extends through said lower conductor plug, lower coax, lower waveguide, lower z-neck and lower dielectric disc.

18. The method for sterilizing waste materials of claim 17 wherein the lower means for dispersing microwave energy comprises:

a generally tubular adaptor having a first end, a second end, a first inside surface adjacent to the first end and defining a first inside diameter, a second inside surface adjacent to the second end and defining a second inside diameter smaller than the first inside diameter, a first annular shoulder joining the first inside surface and the second inside surface, a first outside surface adjacent to the first end and defining a first outside diameter, a second outside surface adjacent to the second end and defining a second outside diameter smaller than the first outside diameter, a second annular shoulder joining the first outside surface and the second outside surface, and a longitudinal axis, said first inside diameter substantially the same as the first outside diameter of said lower dielectric disc so as to closely receive said lower dielectric disc, said second inside diameter substantially the same as the diameter of the hole in the bottom end of said lower z-neck, said first outside diameter smaller than the diameter of the inside surface of said lower z-neck such that the lower dielectric disc and the adapter nest within said lower z-neck;

a lower inner liner having a longitudinal axis comprising
  a substantially tubular shaped portion having an inside surface, an outside surface, and a first flanged end,
  a parabolic shaped bell portion connected to the tubular shaped portion at a point of transition and having a first end defining an inside diameter smaller than an inside diameter of said tubular shaped portion, an inside surface and an outside surface,
  wherein the outside surface of said parabolic shaped bell portion at the first end is closely received by the first inside surface of said adaptor; and
  wherein the flanged end of the tubular shaped portion nests against the flanged top end of said lower outer shell; and a lower deflector having a first end, a second end, a first generally frustoconically shaped outside surface adjacent to the first end, a second generally frustoconically shaped outside surface adjacent to the second end, a third generally cylindrical outside surface connecting the first outside surface and the second outside surface, and a longitudinal axis, said first frustoconically shaped outside surface converging away from the first end at an angle of between about 8 degrees and 25 degrees, said second frustoconically shaped outside surface converging away from the second end at an angle between about 8 degrees and 25 degrees, said second frustoconically shaped outside surface substantially mirroring said first frustoconically shaped outside surface, said second end connected to the second end of said coaxial tube;

wherein the outside surfaces of said tubular shaped portion and said parabolic shaped bell portion of said inner liner are adjacent to the inside surface of said outer lower shell;

wherein the longitudinal axes of said lower outer shell, lower coaxial tube, adaptor, lower inner liner and deflector are coaxial; and wherein said lower coaxial tube extends through said adapter, parabolic shaped bell portion of said inner liner and deflector.

19. The method for sterilizing waste materials of claim 18 wherein the microwave waste sterilizer further comprises:

a disc shaped support tray positioned to support said waste container within said microwave waste sterilizer, said support tray having the characteristic of being substantially transparent to microwaves; and a means for external control.

20. The method for sterilizing waste materials of claim 19 wherein said upper wave guide has a first movable end block and a second movable end block, each said movable end block having the characteristic of a tuning short;

said lower wave guide has a first movable end block and a second movable end block, each said movable end block having the characteristic of a tuning short;

the position of said upper conductor plug is adjustable within said first upper coax and said upper conductor plug has the characteristic of a tuning short; and the position of said lower conductor plug is adjustable within said lower coax and said lower conductor plug has the characteristic of a tuning short.

21. The method for sterilizing waste materials of claim 20 wherein said clamp releasably connects the bottom flanged end of said upper outer shell and the top flanged end of said lower outer shell such that the upper and lower coaxial tubes are aimed at each other and the longitudinal axis of said upper coaxial tube coincides with the longitudinal axis of said lower coaxial tube, said clamp further allowing the clamped microwave waste sterilizer to maintain an internal pressure between 0.138 MPa (20 psig) and 1.38 MPa (200 psig).

22. The method for sterilizing waste materials of claim 21 wherein the upper dielectric disc, conic support, lower dielectric disc, and support tray comprise virgin polytetrafluoroethylene.

23. The method for sterilizing waste materials of claim 21 wherein the upper inner liner, lower inner liner, and deflection cone comprise aluminum and wherein the parabolic bell shapes of the upper liner and lower liner are formed by spinning.

24. The method for sterilizing waste materials of claim 21 further comprising injecting said water in a pre-determined number of batches;

trapping said water and any condensate;

recycling said water and said condensate as injectant.

25. A method for dispersing microwave energy into a chamber, said method comprising:

broadcasting microwave energy across a chamber;

reflecting said microwave energy from a surface of said chamber;

coupling said microwave energy onto a means for coaxial guidance;

changing a first direction of flow of said microwave energy to a second direction of flow substantially parallel to said means for coaxial guidance;

propagating said microwave energy in said second direction of flow within a means for guiding microwave energy;

splitting said microwave energy in a means for dispersing microwave energy; and broadcasting the dispersed microwave energy into a chamber in a flux field of substantially uniform flux, wherein the microwave energy is split into at least two paths by said means for dispersing microwave energy, wherein the flux field is substantially in the shape of a substantially solid cone, wherein said chamber comprises:

a substantially rectangular box shaped waveguide having a first side plate having an outside surface, a first end and a second end, a second side plate substantially parallel to said first side plate and having an outside surface, a first movable end block substantially normal to said first and second side plates and a second movable end block substantially parallel to said first movable side plate, said first side defining a first hole between the first end and a center of said first side plate and a second hole near the second end having a diameter smaller than a diameter of the first hole, said second side plate defining a hole of a diameter substantially the same as the diameter of the first hole in said first side plate, said hole in said second side plate further oriented in axial alignment with the first hole in said first side plate, said first movable end block and said second movable end block each having the characteristic of a tuning short;

a magnetron connected to the first side plate of the waveguide at the second hole so that waves produced by said magnetron are broadcast within said rectangular box shaped waveguide;

a tubular coax having a first end, a second end, an inside surface defining a diameter substantially the same as the diameter of the first hole in the first side plate of said waveguide, and a longitudinal axis, said first end connected to the outside surface of said first side plate so that the longitudinal axis is coaxial with the first hole in said first side plate and the coax is in covering relationship to the first hole in said first side plate; and a tubular conductor plug having a first end, a second end, an outside diameter substantially the same as the inside diameter of said coax, an inside surface defining a diameter substantially the same as the outside diameter of said coaxial tube, and a longitudinal axis, said conductor plug closely received by the second end of said coax;

wherein the position of said conductor plug is adjustable within said coax and said conductor plug has the characteristic of a tuning short.

26. The method for dispersing microwave energy of claim 25 wherein said means for coaxial guidance comprises a coaxial tube having an outside surface, a first end, a second end, an outside diameter and a longitudinal axis.

27. The method for dispersing microwave energy of claim 26 wherein said means for guiding microwave energy comprises:

a substantially can shaped z-neck having a first end, a flange end, a longitudinal axis, and a generally tubular sidewall having an outside surface connecting the first end and the flanged end and an inside surface defining a diameter greater than the diameter of the hole in the second side plate of said waveguide, said first end defining a hole coaxial with the longitudinal axis and having a diameter substantially the same as a diameter of the hole in said second side plate of said waveguide, said flange end being substantially ring shaped and having a generally cylindrical inside surface coincident with the inside surface of said z-neck, said first end connected to the second side plate of said waveguide so that the hole in the first end is coaxial with the hole in said second side plate and said first end is in covering relationship with the hole in said second plate; and a generally tubular dielectric disc having a first end, a second end, a longitudinal axis, a first outside surface adjacent to the first end and defining a first outside diameter, a second outside surface adjacent to the second end and defining a second outside diameter which is greater than the first outside diameter, a first annular shoulder joining the first outside surface and the second outside surface, and an inside surface defining a diameter substantially the same as the outside diameter of said coaxial tube, said dielectric disc having the characteristic of being substantially transparent to microwaves, said dielectric disc positioned in z-neck in covering relationship with the hole in the first end of said z-neck.

28. The method for dispersing microwave energy of claim 27 wherein said means for dispersing microwave energy comprises:

a generally tubular adaptor having a first end, a second end, a first inside surface adjacent to the first end and defining a first inside diameter, a second inside surface adjacent to the second end and defining a second inside diameter smaller than the first inside diameter, a first annular shoulder joining the first inside surface and the second inside surface, a first outside surface adjacent to the first end and having a first outside diameter, a second outside surface adjacent to the second end and defining a second outside diameter smaller than the first outside diameter, a second annular shoulder joining the first outside surface and the second outside surface, and a longitudinal axis, said first inside diameter substantially the same as the first outside diameter of said dielectric disc so as to closely receive said dielectric disc, said second inside diameter substantially the same as the diameter of the hole in the first end of said z-neck, said first outside diameter smaller than the diameter of the inside surface of said z-neck such that the dielectric disc and the adapter nest within said z-neck;

a generally bowl shaped outer shell having an inside surface, an outside surface, and a longitudinal axis, said outer shell further defining a hole at an apex of the bowl shape, said outside surface connected to the flange end of said z-neck so that the z-neck is in covering relationship to the hole in the apex of the bell shape of said outer shell;

an inner liner having a longitudinal axis comprising
a substantially tubular shaped portion having an inside surface and an outside surface, and
a parabolic shaped bell portion connected to the tubular shaped portion at a point of transition and having a first end defining an inside diameter smaller than an inside diameter of said tubular shaped portion, an inside surface and an outside surface, said outside surface at the first end closely received by the first inside surface of said adaptor, wherein the outside surfaces of said tubular shaped portion and said parabolic shaped bell portion of said inner liner are adjacent to the inside surface of said outer shell; and a deflector having a first end, a second end, a first generally frustoconically shaped outside surface adjacent to the first end, a second generally frustoconically shaped outside surface adjacent to the second end, a third generally cylindrical outside surface connecting the first outside surface and the second outside surface, and a longitudinal axis, said first frustoconically shaped outside surface converging away from the first end at an angle of between about 8 degrees and 25 degrees, said second frustoconically shaped outside surface converging away from the second end at an angle between about 8 degrees and 25 degrees, said second frustoconically shaped outside surface substantially mirroring said first frustoconically shaped outside surface, said second end connected to the second end of said coaxial tube.

29. The method for dispersing microwave energy of claim 28 wherein the longitudinal axes of said outer shell, coaxial tube, coax, conductor plug, z-neck, dielectric disc, adaptor, inner liner and deflector are coaxial; and wherein said coaxial tube extends through said conductor plug, coax, waveguide, z-neck, dielectric disc, adapter, parabolic shaped bell portion of said inner liner and deflector.

30. The method for dispersing microwave energy of claim 29 wherein a first path for microwave energy is formed by the inside surfaces of said tubular shaped portion and said parabolic shaped bell portion of said inner liner, and a second path is formed by said coaxial tube.

* * * * *

UNITED STATES PATENT AND TRADEMARK OFFICE
CERTIFICATE OF CORRECTION

PATENT NO.   : 5,728,310
DATED        : March 17, 1998
INVENTOR(S)  : Charles L.. Ice, et al.

It is certified that error appears in the above-identified patent and that said Letters Patent is hereby corrected as shown below:

On the title page, item[73] Assignee, should read—United Systems, Inc., Arlington, TX.--

Signed and Sealed this

Twenty-ninth Day of September, 1998

*Attest:*

BRUCE LEHMAN

*Attesting Officer*     *Commissioner of Patents and Trademarks*